United States Patent [19]

Kanno et al.

[11] 4,190,502
[45] Feb. 26, 1980

[54] METHOD OF EVALUATING THE CORROSION RATE OF METAL

[75] Inventors: Ken-ichi Kanno; Masayuki Suzuki, both of Yokohama; Yuichi Sato, Atsugi; Masamichi Machida, Fuchu, all of Japan

[73] Assignee: Tokyo Shibaura Denki Kabushiki Kaisha, Kawasaki, Japan

[21] Appl. No.: 950,051

[22] Filed: Oct. 10, 1978

[30] Foreign Application Priority Data

Oct. 7, 1977 [JP] Japan .................. 52-120779

[51] Int. Cl.² ............... G01N 27/46; G01N 27/30
[52] U.S. Cl. ........................... 204/1 T; 204/195 C
[58] Field of Search ..................... 204/1 C, 195 C

[56] References Cited

U.S. PATENT DOCUMENTS

| | | | |
|---|---|---|---|
| 4,056,445 | 11/1977 | Gauntt et al. | 204/1 C |
| 4,130,464 | 12/1978 | Kanno et al. | 204/1 C |

OTHER PUBLICATIONS

S. Barnartt, "Two-Point & Three-Point Methods for the Investigation of Electrode Reaction Mechanisms", *Electrochimica Acta*, vol. 15, pp. 1313–1324 (1970).
P. Delahay, "Coulostatic Method for the Kinetic Study of Fast Electrode Processes, I. Theory", *J. Physchem.*, vol. 66, pp. 2204–2207 (1962).
J. L. Ord et al., "The Anodic Oxidation of Iron: Overpotential Analysis for a Two-Phase Film", *J. Electrochem. Soc.*, vol. 123, pp. 1876–1882 (1976).
M. Prazak, "The Polarization Resistance Method for Corrosion Testing", *Werkstoffe und Korrosion*, vol. 25, pp. 104–112 (1974).
P. J. Moreland et al., "Technique & Instrumentation for Polarization Resistance Measurements", *Br. Corrosion Journal*, vol. 12, pp. 72–79 (1977).

*Primary Examiner*—Aaron Weisstuch
*Attorney, Agent, or Firm*—Oblon, Fisher, Spivak, McClelland & Maier

[57] ABSTRACT

A metal test piece is disposed in a cell filled with a test solution. The metal test piece is electrically charged instantaneously through a counter electrode so as to have a few millivolts polarization potential $\eta_t$. The charge consumed by the corrosion reaction of the test piece is measured by a potential recorder in the form of a variation of the polarization potential $\eta_t$ with respect to time t. The measured ($\eta_t$-t) relation is analyzed to obtain a polarization resistance $R_P$ of the metal test piece. After the potential of the metal test piece returns to its natural potential Ecorr, the test piece is charged again until its polarization potential $\eta_t$ rises to 50 millivolts or more, and the ($\eta_t$-t) relation is measured in the same way as mentioned above. Based on this relation, the Tafel slope $\beta_a$ of the anodic reaction is obtained. After the potential of the metal test piece has returned to its natural potential Ecorr, the test piece is so charged for the third time as to have its polarization potential $\eta_t$ lowered to $-50$ millivolts or less, and the ($\eta_t$-t) relation is measured. This relation is analyzed to obtain the Tafel slope $\beta_c$ of the cathodic reaction. Based on the polarization resistance $R_P$, Tafel slopes $\beta_a$ and $\beta_c$, the corrosion current density $I_{corr}$ is obtained, from which the corrosion rate V is calculated.

19 Claims, 14 Drawing Figures

$\eta t - t$ CURVE log $\eta t - t$ CURVE

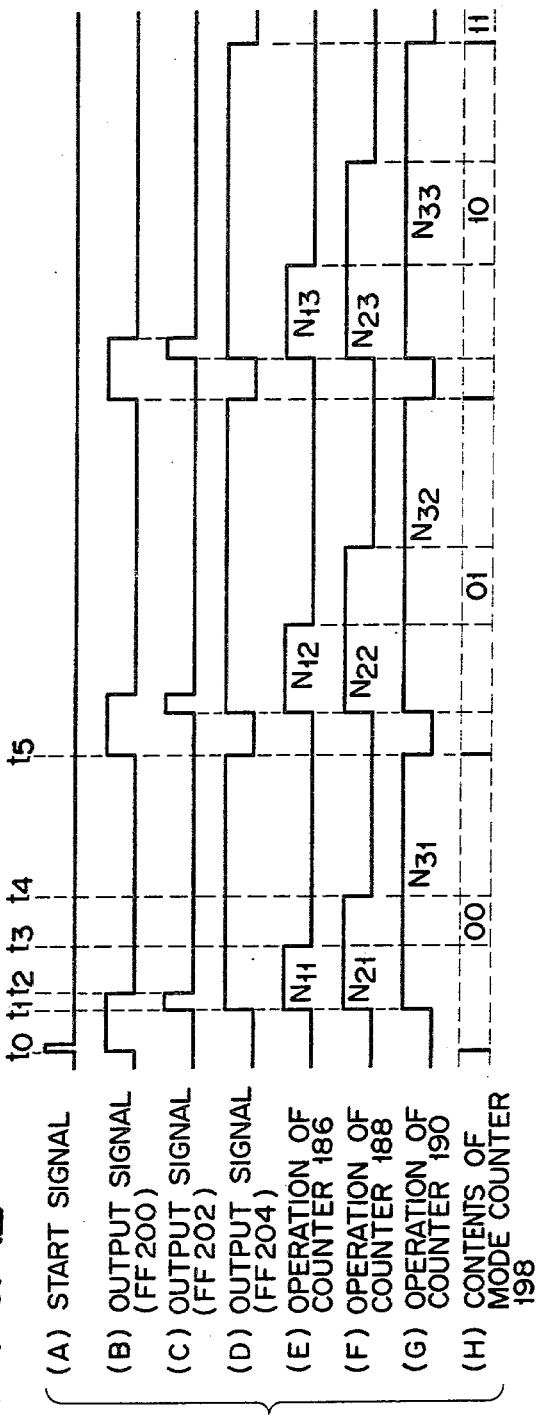
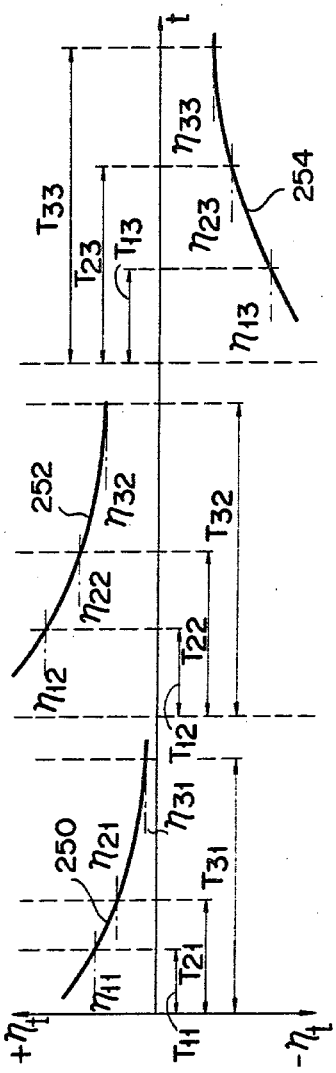

METHOD OF EVALUATING THE CORROSION RATE OF METAL

This invention relates to a method of evaluating the corrosion rate of metal, using coulostatic techniques.

A method of evaluating the corrosion rate of metal has been proposed by the inventors and disclosed in U.S. Patent Application Ser. No. 798,168 filed May 18, 1977, now U.S. Pat. No. 4,130,464. The present invention is an improvement of the invention disclosed in the U.S. Patent application.

In the method according to the above-mentioned U.S. Patent, the polarization resistance $R_p$ of a metal test piece is obtained. Since the polarization resistance $R_p$ is inversely proportional to the corrosion rate V of the test piece, the corrosion rate V is evaluated, if necessary, by the following equations (1) and (2):

$$V = (M/Z \cdot F) \cdot I_{corr} \qquad (1)$$

$$I_{corr} = (K/2 \cdot 3)/R_p \qquad (2)$$

In equation (1), $I_{corr}$ denotes the corrosion current density, M the atomic weight of the test piece, Z the valence of the dissolved metal ion, and F the Faraday constant. In equation (2), K denotes the constant inherent to the corrosion reaction and is equal to: $\beta_a \cdot \beta_c / (\beta_a + \beta_c)$, where $\beta_a$ and $\beta_c$ denote the Tafel slopes of anodic and cathodic reactions, respectively.

The specification of the above-mentioned U.S. Patent describes in detail how to obtain the polarization resistance $R_p$. However it does not show how to obtain Tafel slopes $\beta_a$ and $\beta_c$ or how to obtain the corrosion current density $I_{corr}$ based on the Tafel slopes $\beta_a$ and $\beta_c$. Indeed it is possible to estimate the corrosion rate V from the polarization resistance $R_p$. But this is not a fully reliable method of evaluating the corrosion rate of metal. Although Tafel slopes $\beta_a$ and $\beta_c$ do not influence the corrosion rate V so much, they differ according to the kinds of metals which are corroded and the corrosion solution. Thus, if the corrosion rate V is estimated directly from the polarization resistance $R_p$ without taking the Tafel slopes into account, there will be an error in the estimated corrosion rate V. In order to evaluate the corrosion rate V accurately, the polarization resistance $R_p$ and Tafel slopes $\beta_a$ and $\beta_c$ of the same metal test piece should be measured under substantially the same condition, thereby to obtain the corrosion current density $I_{corr}$.

A method of measuring the polarization resistance $R_p$ and Tafel slopes $\beta_a$ and $\beta_c$ of a metal test piece is known, wherein the potential of the test piece is varied gradually or a relatively large constant current is made to flow through the test piece and the test solution in which the test piece is immersed. This method, however, is defective in the following respects. First, if the test solution has a large resistance, an error may be made in the results due to an ohmic drop. Second, in most cases it takes a long time until the potential of the test piece reaches an equilibrium or steady state value if a constant current is made to flow through the test piece in the test solution or until the current flowing through the test piece reaches a steady value if a constant potential is applied to the test piece. During such a long time, the surface condition of the test piece may change to such an extent as to make it difficult to correctly measure the polarization resistance $R_p$ and Tafel slopes $\beta_a$ and $\beta_c$. Third, it also takes a long time to obtain a Tafel slope, and the method is therefore not desirable from a practical point of view. Indeed a potential sweep method may be used, thereby to shorten the times necessary for obtaining one Tafel slope, but it seems difficult with this method to obtain an accurate Tafel slope.

An object of this invention is to provide a method of evaluating the corrosion rate of metal, wherein the polarization resistance $R_p$ and Tafel slopes $\beta_a$ and $\beta_c$ of a metal test piece are measured by the same device under substantially the same condition and then quickly and accurately analyzed to obtain a corrosion current density $I_{corr}$ which is proportional to the corrosion rate V of the metal test piece.

This invention provides a method of evaluating the corrosion rate of metal in a corrosive solution, comprising:

(A) the step of determining the polarization resistance $R_p$ of a metal test piece having a surface area S and disposed in a corrosive solution, said step comprising:
  (i) instantaneously feeding a given amount of charge $q_{Rp}$ to the electrical double layer of the metal test piece, thereby changing the potential of the metal test piece to have a predetermined polarization potential $\eta_{Rp}$;
  (ii) detecting, as a function of time, the variation of the polarization potential $\eta_{Rp}(t)$ of the test piece due to a corrosion reaction, using a reference electrode disposed in the corrosive solution;
  (iii) estimating an initial polarization potential $\eta_{Rp}(o)$ of the test piece upon completion of the charge supply (t=0), based on the polarization potential $\eta_{Rp}(t)$ detected as a function of time; and
  (iv) calculating the polarization resistance $R_p$ based on the given charge $q_{Rp}$, initial polarization potential $\eta_{Rp}(0)$, surface area S, and the slope of the log $(\eta_{Rp}(t)\text{-}t)$ relation, (B) the step of determining the Tafel slope $\beta_a$ of anodic reaction of the metal test piece, said step comprising:
  (i) instantaneously feeding the electrical double layer of the test piece with a charge $q_{\beta a}$ whose absolute value is larger than that of charge $q_{Rp}$, thereby changing the potential of the metal test piece to have a predetermined polarization potential $\eta_{\beta a}$ whose value is positive and higher than the polarization potential $\eta_{Rp}$;
  (ii) detecting, as a function of time, the variation of the polarization potential $\eta_{\beta a}(t)$ of the test piece due to a corrosion reaction, using the reference electrode; and
  (iii) calculating the Tafel slope $\beta_a$ of the test piece based on the polarization potential $\eta_{\beta a}(t)$ of the metal test piece detected as a function of time, (C) the step of determining the Tafel slope $\beta_c$ of cathodic reaction of the metal test piece, said step comprising:
  (i) instantaneously feeding the electrical double layer of the test piece with a charge $q_{\beta c}$ whose absolute value is larger than that of the charge $q_{Rp}$ and whose polarity is opposite to that of the charge $q_{\beta a}$, thereby changing the potential of the test piece to have a predetermined polarization potential $\eta_{\beta c}$ whose value is negative;
  (ii) detecting, as a function of time, the variation of the polarization potential $\eta_{\beta c}(t)$ of the test piece due to a corrosion reaction, using the reference electrode; and (iii) calculating the Tafel slope $\beta_c$ of the metal test piece based on the polarization potential $\eta_{\beta c}$ (t) of the metal test piece detected as a function of time, and (D) the step of calculating the corrosion current density $I_{corr}$ of the metal test piece based on the polarization resistance $R_p$, Tafel slope $\beta_a$ and Tafel slope $\beta_c$.

This invention can be more fully understood from the following detailed description when taken in conjunction with the accompanying drawings, in which.

Figure 10A:
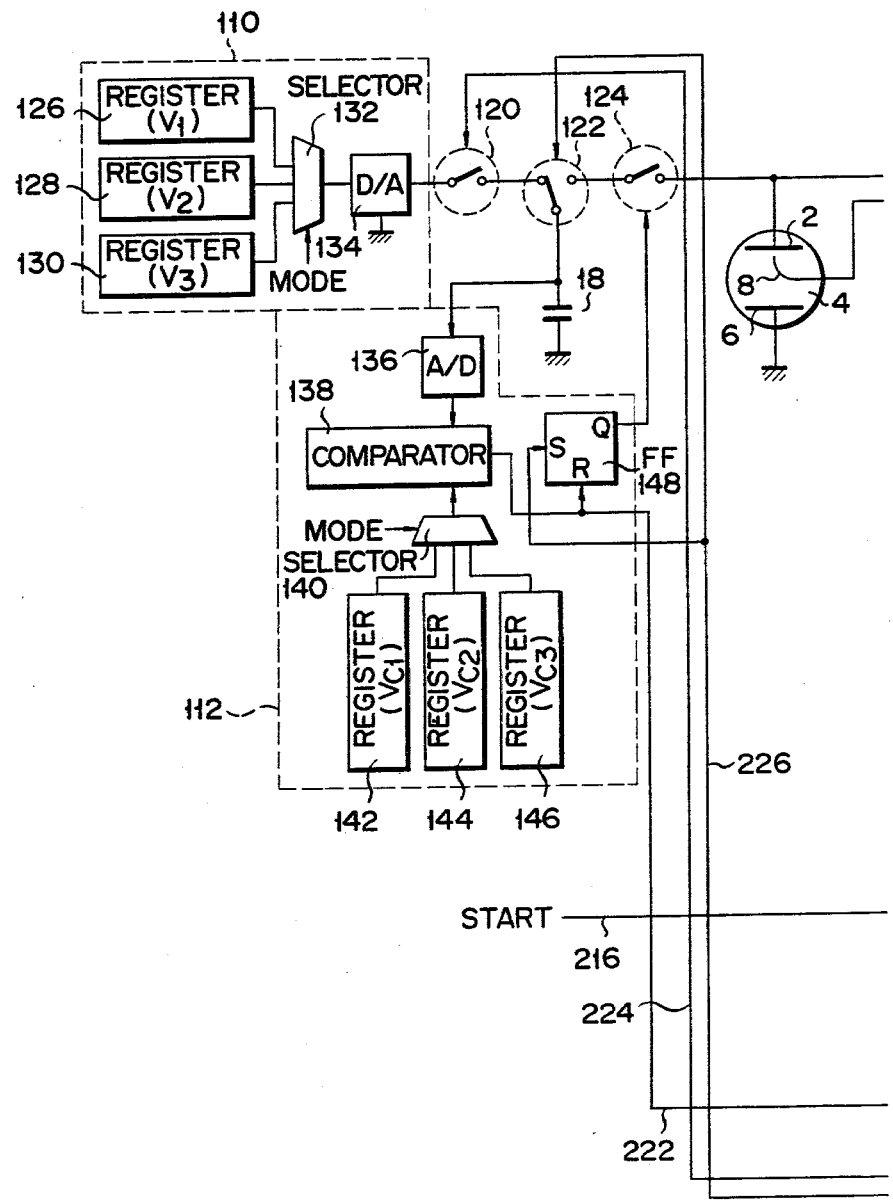
Figure 10B:
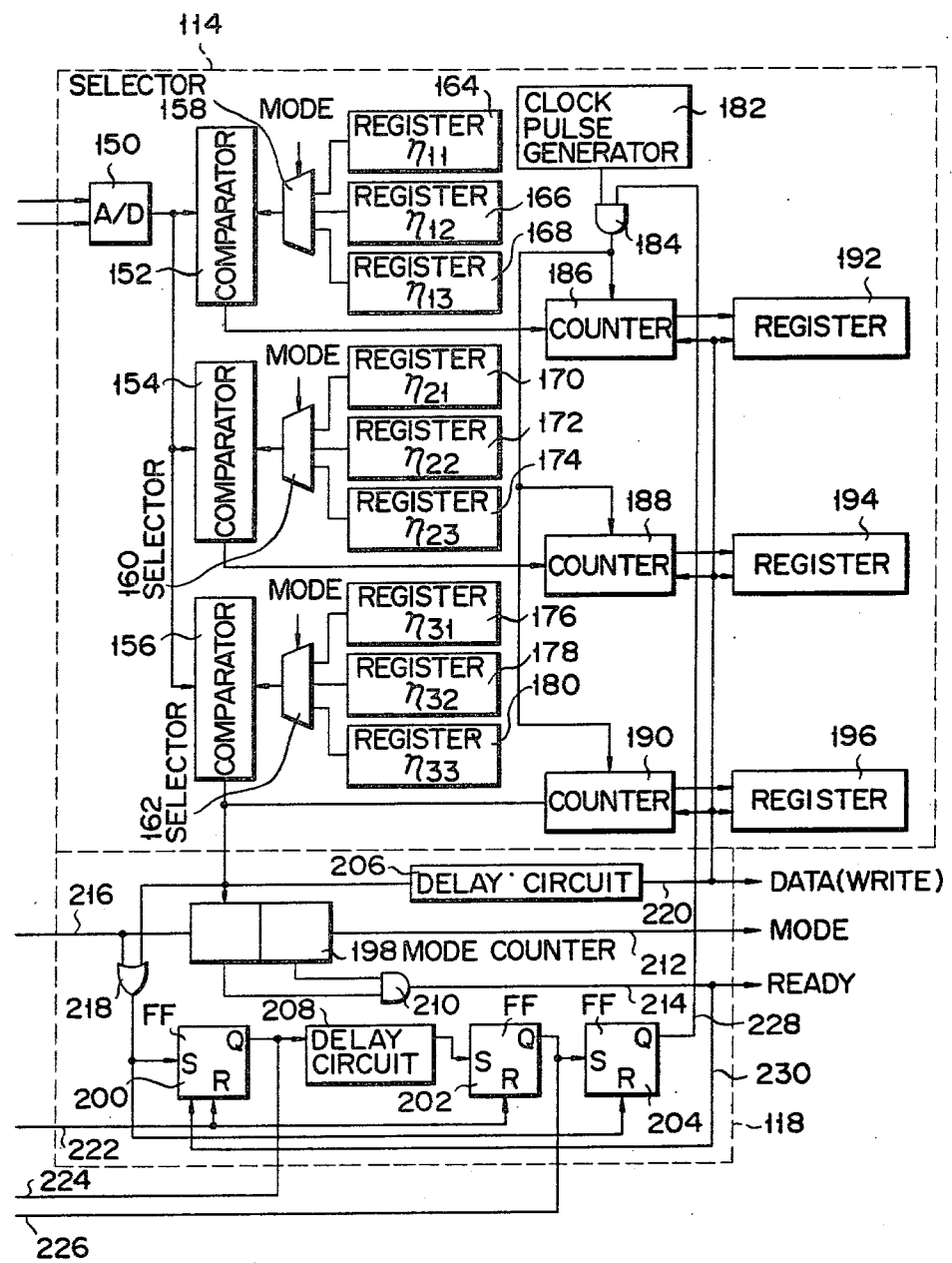
Figure 11:
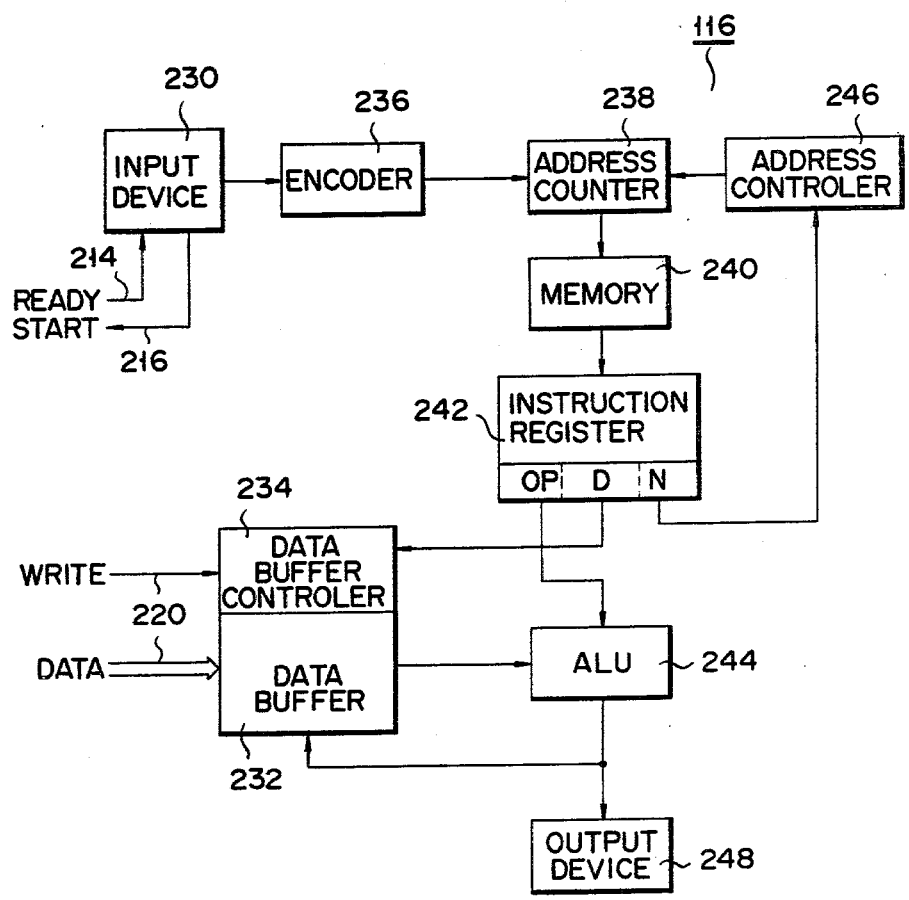

FIGS. 10A, 10B and 11 are block diagrams each showing a measuring apparatus including a data analyzing device for the method of evaluating the corrosion rate of metal according to this invention; and FIGS. 12 and 13 are time charts illustrating the operation of the measuring apparatus shown in FIGS. 10A, 10B and 11 and corresponding $\eta$-t curves.

Figure 1:
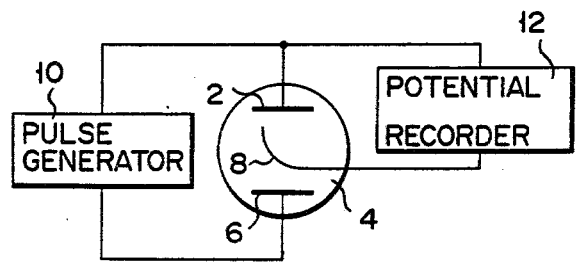
FIG. 1 is a block diagram of a suitable measuring apparatus for carrying out the method of evaluating the corrosion rate of metal according to this invention.

The measuring apparatus shown in FIG. 1 measures the relationship between lapse of time t and the polarization potential $\eta_t$ of a metal test piece 2. The test piece 2 is charged three times with different charges, thereby to obtain three $\eta_t$-t curves showing the relationship between the lapse of time t and the polarization potential $\eta_t$. These $\eta_t$-t curves are analyzed to obtain the polarization resistance $R_p$ of the test piece, Tafel slope $\beta_a$ of anodic reaction of the test piece and Tafel slope $\beta_c$ of cathodic reaction of the test piece.

The measuring apparatus is provided with a cell 4 filled with a test solution such as distilled water. The surface area S of the metal test piece 2 is measured, and the test piece 2 is put into the cell 4 and immersed in the test solution. The metal test piece 2 acts as a working electrode. A counter electrode 6 is disposed in the cell 4 in such a position as to face the test piece 2. A reference electrode 8 is arranged between the test piece 2 and the counter electrode 6. A pulse generator 10 is connected between the test piece 2 and the counter electrode 6 to supply a predetermined charge. A potential recorder 12 is connected between the test piece 2 and the reference electrode 8 to detect the polarization potential $\eta_t$ of the test piece 2. The recorder 12 has a high input impedance.

The potential recorder 12 records, as mentioned above, three $\eta_t$-t curves. A first $\eta_t$-t curve is analyzed to obtain the polarization resistance $R_p$ of the test piece 2, a second $\eta_t$-t curve to obtain Tafel slope $\beta_a$, and the third $\eta_t$-t curve to obtain Tafel slope $\beta_c$.

Figure 2:
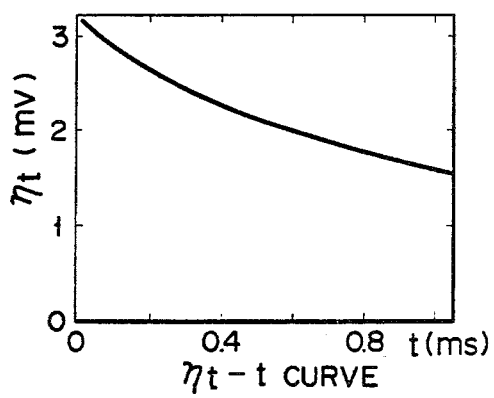
FIGS. 2 and 3 are graphs showing the relationship between the lapse of time t and the polarization potential $\eta_t$ measured by the method according to this invention.
Figure 3:
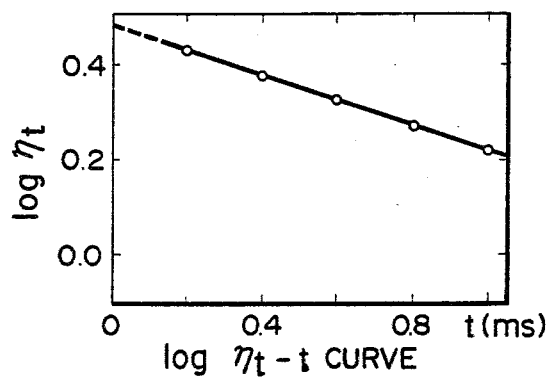

First it will be described how to record the first $\eta_t$-t curve and how to obtain the polarization resistance $R_p$. Via the counter electrode 6, a predetermined charge $q_1$ is applied to the test piece 2 for a short time such as several microseconds to a few milliseconds, thus instantaneously charging the electrical double layer of the test piece 2. The charge $q_1$ is of such a positive or negative value as to change the polarization potential $\eta_t$ of the test piece 2 by not more than 30 millivolts, preferably 10 millivolts or less. The charge $q_1$ on the electrical double layer is consumed by a corrosion reaction of the test piece 2. As a result, the potential of the test piece 2 varies gradually to the natural potential, i.e. corrosion potential $E_{corr}$. This potential variation is detected by use of the reference electrode 8 and recorded by the potential recorder 12, thereby providing on $\eta_t$-t curve such as shown in FIG. 2 and a log $\eta_t$-t curve such as shown in FIG. 3.

The polarization potential $\eta_t$ is expressed as follows:

$$\eta_t = \eta_O \exp(-t/C_D R_p) \qquad (3)$$

In equation (3), $\eta_O$ denotes the initial polarization potential of the test piece 2, and $C_d$ the differential capacitance of the test piece 2. Equation (3) may be transformed into the following logarithmic equation:

$$\log \eta_t - \log \eta_O = -t/C_D R_p \qquad (4)$$

The differential capacitance $C_D$ can be represented as follows:

$$C_D = \Delta q_1/\eta_O = q_1/S \cdot \eta_O \qquad (5)$$

Equation (4) represents a rectilinear line and the log $\eta_t$-t curve is linearly plotted on a semilogarithmic graph shown in FIG. 3. Thus, the initial potential $\eta_O$ of the test piece 2 is obtained by extrapolating the rectilinear line to the initial potential $\eta_O$. The differential capacitance $C_D$ is obtained by substituting the intitial polarization potential $\eta_O$ into equation (5). Since the slope $-1/C_D R_p$ can be obtained from the log $\eta_t$-t curve, the polarization resistance $R_p$ is determined. The specification of U.S. Pat. No. 4,130,464 describes in detail how to obtain the polarization resistance $R_p$.

Figure 4:
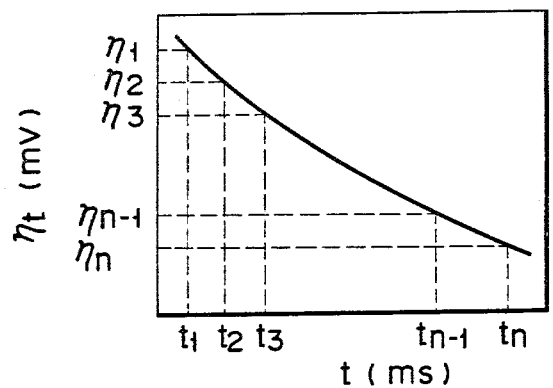
FIG. 4 is a graph showing the relationship between lapse of time t and polarization potential $\eta_t$.

Now it will be described how to record the second $\eta_t$-t curve from which Tafel slope $\beta_a$ is to be obtained. Via the counter electrode 6 a predetermined charge $q_2$ is applied to the test piece 2 for a short time, for example several microseconds to a few milliseconds, thus instantaneously charging the electrical double layer of the test piece 2. The charge $q_2$ is larger than the charge $q_1$ applied to the test piece in order to obtain the polarization resistance $R_p$. More specifically, the charge $q_2$ is of such a value as to elevate the polarization potential $\eta_t$ of the test piece 2 not less than 30 millivolts, preferably 50 millivolts or more. The charge $q_2$ is used up by the corrosion reaction of the working electrode and the potential of the test piece 2 gradually varies. This potential variation is detected by using the reference electrode 8 and recorded by the potential recorder 12, thereby obtaining such a $\eta_t$-t curve as shown in FIG. 4.

In a similar way, the third $\eta_t$-t curve from which Tafel slope $\beta_c$ is to be obtained is recorded. Namely, a predetermined charge $q_3$ of the opposite polarity to the charge $q_2$ is applied through the counter electrode 6 to the test piece 2 for a short time, for example, several microseconds to a few milliseconds. The charge $q_3$ is of such a value as to lower the polarization potential $\eta_t$ of the test piece 2 to not more than $-30$ millivolts, preferably to $-50$ millivolts or lower.

The three $\eta_t$-t curves need not be obtained in the above-mentioned order. However it is desired that charge not be applied to the test piece 2 until the potential of the test piece 2 returns to the natural potential, i.e.

corrosion potential $E_{corr}$. To bring the potential of the test piece 2 quickly back to the corrosion potential $E_{corr}$, a backward bias may be applied to the test piece 2.

It will now be explained how to obtain the Tafel slope $\beta_a$ of anodic reaction and the Tafel slope $\beta_c$ of cathodic reaction, respectively from the second and third $\eta_t$-t curves.

The corrosion reaction of the test piece 2 can be expressed basically by the following equation:

$$I/I_{corr} = \exp(2.3/\beta_a \eta_t) - \exp(2.3/\beta_c \eta_t) \quad (6)$$

In equation (6), I denotes faradaic current density, and $I_{corr}$ corrosion current density. If the polarization potential $\eta_t$ is not more than 30 millivolts, equation (3) is derived as an $\eta_t$-t relation. Thus, in order to measure the polarization resistance $R_p$ accurately, the polarization potential $\eta_t$ is changed by a few millivolts, or no more than 10 millivolts.

If the polarization potential $\eta_t$ of the test piece 2 is changed to not less than 30 millivolts, preferably to 50 millivolts or more in order to obtain the Tafel slope $\beta_a$ of anodic reaction, equation (6) is simplified as follows:

$$I = I_{corr}(2.3/\beta_a \eta_t) \quad (7)$$

Suppose charge $q_2$, which satisfies equation (7), is applied to the test piece 2 at the corrosion potential $E_{corr}$ and that the polarization potential of the test piece 2 rises to $\eta_m$. Then, the polarization potential gradually varies as time elapses. A specific polarization potential $\eta_i$ is selected, which is represented as: $0 < \eta_i < \eta_m$. When the polarization potential varies to $\eta_i$, the time count is started again. If the differential capacitance $C_d$ remains constant over the period of time t in which the polarization potential varies from $\eta_i$ to $\eta_t$, then the charge consumed during the period $\Delta q_{O \to t}$ can be represented as follows:

$$\widetilde{\Delta q}_{O \to t} = C_d(\eta_i - \eta_t) \quad (8)$$

Faradaic current density I in equation (7) corresponds to the current which has flown during the corrosion reaction. Thus, if this current I is integrated over time t, the consumed charge $\Delta q_{O \to t}$ is equal to the integrated value of the current I. That is:

$$\widetilde{\Delta q}_{O \to t} = \int_0^t I dt = \int_0^t I_{corr} \cdot \exp(\frac{2.3}{\beta_a} \eta_t) dt \quad (9)$$

Equations (8) and (9) are differentiated into the following equation:

$$-C_d d\eta_t/dt = I_{corr} \exp(2.3/\beta_a \eta_t) \quad (10)$$

Differential equation (10) is solved, under the initial condition of $\eta_t = \eta_i$ at $t = 0$. Then, the following equation is obtained:

$$\exp(-\frac{2.3}{\beta_a} \eta_t) = \frac{I_{corr}}{C_d} t \times \frac{2.3}{\beta_a} + \exp(-\frac{2.3}{\beta_a} \eta_i) \quad (11)$$

If three polarization potentials $\eta_1$, $\eta_2$ and $\eta_3$ of the test piece 2 at different times $t_1$, $t_2$ and $t_3$ are read from the $\eta_t$-t curve in FIG. 4, the following three equations are established:

$$\exp(-\frac{2.3}{\beta_a} \eta_1) = \frac{I_{corr}}{C_d} \times \frac{2.3}{\beta_a} t_1 + \exp(-\frac{2.3}{\beta_a} \eta_i) \quad (12)$$

$$\exp(-\frac{2.3}{\beta_a} \eta_2) = \frac{I_{corr}}{C_d} \times \frac{2.3}{\beta_a} t_2 + \exp(-\frac{2.3}{\beta_a} \eta_i) \quad (13)$$

$$\exp(-\frac{2.3}{\beta_a} \eta_3) = \frac{I_{corr}}{C_d} \times \frac{2.3}{\beta_a} t_3 + \exp(-\frac{2.3}{\beta_a} \eta_i) \quad (14)$$

Subtracting equation (13) from equation (12), the following equation is established:

$$\exp(-\frac{2.3}{\beta_a} \eta_1) - \exp(-\frac{2.3}{\beta_a} \eta_2) = \frac{I_{corr}}{C_d} \cdot \frac{2.3}{\beta_a} (t_1 - t_2) \quad (15)$$

Subtracting equation (14) from equation (13), the following equation is established:

$$\exp(-\frac{2.3}{\beta_a} \eta_2) - \exp(-\frac{2.3}{\beta_a} \eta_3) = \frac{I_{corr}}{C_d} \cdot \frac{2.3}{\beta_a} (t_2 - t_3) \quad (16)$$

If equation (15) is divided by equation (16), the result is as follows:

$$\frac{\exp(-\frac{2.3}{\beta_a} \eta_1) - \exp(-\frac{2.3}{\beta_a} \eta_2)}{\exp(-\frac{2.3}{\beta_a} \eta_2) - \exp(-\frac{2.3}{\beta_a} \eta_3)} = \frac{t_1 - t_2}{t_2 - t_3} \quad (17)$$

Equation (17) shows that Tafel slope $\beta_a$ of anodic reaction can be obtained if the polarization potentials $\eta_1$, $\eta_2$ and $\eta_3$ at three different times $t_1$, $t_2$ and $t_3$ are read. Suppose $\eta_1 < \eta_2 < \eta_3$, $\eta_1 = \eta_2 + \Delta\eta$ and $\eta_3 = \eta_2 - \Delta\eta (\Delta\eta < 0)$ and that $\Delta\eta$ is therefore equal to $\eta_1 - \eta_2$ and $\eta_2 - \eta_3$. Then, the left term of equation (17) can be simplified as follows:

$$\text{(THE LEFT TERM)} = \frac{\exp\{-\frac{2.3}{\beta_a}(\eta_2 + \Delta\eta)\} - \exp(-\frac{2.3}{\beta_a} \eta_2)}{\exp(-\frac{2.3}{\beta_a} \eta_2) - \exp\{-\frac{2.3}{\beta_a}(\eta_2 - \Delta\eta)\}}$$

$$= \frac{\exp(-\frac{2.3}{\beta_a} \eta_2)\{\exp(-\frac{2.3}{\beta_a} \Delta\eta) - 1\}}{\exp(-\frac{2.3}{\beta_a}(\eta_2 - \Delta\eta)\{\exp(-\frac{2.3}{\beta_a} \Delta\eta) - 1\}}$$

$$= \frac{\exp(-\frac{2.3}{\beta_a} \eta_2)}{\exp(-\frac{2.3}{\beta_a} \eta_2) \cdot \exp(\frac{2.3}{\beta_a} \Delta\eta)}$$

$$= \frac{1}{\exp(\frac{2.3}{\beta_a} \Delta\eta)}$$

Consequently, $$\frac{1}{\exp(\frac{2.3}{\beta_a} \Delta\eta)} = \frac{t_1 - t_2}{t_2 - t_3} \quad \beta_a = \frac{\Delta\eta}{\log\frac{t_3 - t_2}{t_2 - t_1}} \quad (18)$$

Equation (18) shows that anodic Tafel slope $\beta_a$ can be easily calculated by reading from the $\eta_t$-t curve ($\eta > > 0$) the time $t_2$ at which the potential $\eta_2$ is recorded, the time $t_1$ at which the potential $\eta_1$ higher than $\eta_2$ by $\Delta\eta$ is recorded and the time $t_3$ at which the potential $\eta_3$ lower than $\eta_2$ by $\Delta\eta$ is recorded. In order words, Tafel slope $\beta_a$ is calculated based on only $\Delta\eta$, $t_1$, $t_2$ and $t_3$.

In practice, the Tafel slope $\beta_a$ is calculated accurately in the following way:

Suppose that a $\eta_t$-t curve such as shown in FIG. 4. is obtained, wherein $\eta_t$ is more than 50 milivolts. Polarization potentials $\eta_1, \eta_2, \eta_3, \ldots, \eta_{n-1}$ and $\eta_n$ are selected from the curve, where $\eta_1-\eta_2=\eta_2-\eta_3=\ldots=\eta_{n-1}-\eta_n=\Delta\eta$, and the corresponding times $t_1, t_2, t_3, \ldots, t_{n-1}$ and $t_n$ are read off the time axis. The times are combined to form a first group ($t_1, t_2, t_3$), a second group ($t_2, t_3, t_4$), ..., and the last group ($t_{n-2}, t_{n-1}, t_n$). From these groups the following items are calculated:

$$\frac{t_3-t_2}{t_2-t_1}, \frac{t_4-t_3}{t_3-t_2}, \ldots \frac{t_n-t_{n-1}}{t_{n-1}-t_{n-2}}.$$

The average $\delta$ of these items is calculated as follows:

$$\delta = \frac{1}{n-2}\left(\frac{t_3-t_2}{t_2-t_1} + \frac{t_4-t_3}{t_3-t_2} + \ldots \frac{t_n-t_{n-1}}{t_{n-1}-t_{n-2}}\right) \quad (19)$$

Equation (18) is rewritten into the following equation using the average $\delta$:

$$\beta_a = \Delta\eta/\log\delta \quad (20)$$

In this way anodic Tafel slope $\beta_a$ can be obtained accurately.

In equations (17), (18) and (20) there are no terms including $I_{corr}$ or $C_d$. Thus Tafel slope $\beta_a$ can be easily analyzed from these equations. But, if $\Delta\eta$(i.e. difference between $\eta_1$ and $\eta_2$, between $\eta_2$ and $\eta_3$ and so forth) is set to be relatively large, the differential capacitance $C_d$ may inevitably vary. $\Delta\eta$ should therefore be made sufficiently small, for instance 10 millivolts or less, so that the variation of $C_d$ is negligibly small.

In order to obtain the Tafel slope $\beta_c$ of cathodic reaction, the polarization potential $\eta_t$ is changed to not more than $-30$ millivolts, preferably to $-60$ to $-50$ millivolts or lower. Then the following equation will be established:

$$I = -I_{corr}\exp\left(-\frac{2\cdot3}{\beta_c}\eta\right) \quad (21)$$

Equation (21) is similar to equation (7). Thus, similar equations to equations (8), (9) and (10) are established. And the following equation, which is similar to equation (11), is also established:

$$\exp\left(\frac{2\cdot3}{\beta_c}\eta\right) = \frac{I_{corr}}{C_d}t \times \frac{2\cdot3}{\beta_c} + \exp\left(\frac{2\cdot3}{\beta_c}\eta_i\right) \quad (22)$$

Polarization potentials $\eta_1, \eta_2$ and $\eta_3$ at three different times $t_1, t_2$ and $t_3$ are read from the $\eta_t$-t curve obtained by lowering $\eta_t$ to $-60$ to $-50$ millivolts or lower. If $\eta_1<\eta_2<\eta_3$ and $\eta_1=\eta_2-\Delta\eta, \eta_3=\eta_2+\Delta\eta(\Delta\eta>0)$, then Tafel slope $\beta_c$ can be expressed as follows:

$$\beta_c = \frac{\Delta\eta}{\log\frac{t_1-t_i}{t-t_1}} \quad (23)$$

If many polarization potentials $\eta_1, \eta_2, \eta_3, \ldots \eta_{n-1}$ and $\eta_n$ are selected from the $\eta_t$-t curve where $\eta_2-\eta_1=\eta_3-\eta_2=\ldots\eta_n-\eta_{n-1}=\Delta\eta$, thereby reading out the corresponding times $t_1, t_2, t_3, \ldots t_{n-1}$ and $t_n$, equations similar to equations (19) and (20) will be established. That is, cathodic Tafel slope $\beta_c$ is expressed as follows:

$$\beta_c = \Delta\eta/\log\delta \quad (24)$$

In equation (24) the average $\delta$ is expressed as follows:

$$\delta = \frac{1}{n-2}\left(\frac{t_3-t_2}{t_2-t_1} + \frac{t_4-t_3}{t_3-t_2} + \ldots + \frac{t_n-t_{n-1}}{t_{n-1}-t_{n-2}}\right) \quad (25)$$

Now that the polarization resistance $R_p$, anodic Tafel slope $\beta_a$ and cathodic Tafel slope $\beta_c$ have been obtained in the aforementioned manner, the corrosion current density $I_{corr}$ can be calculated by equation (2): $I_{corr}=(K/2.3)/R_p$, wherein $K=\beta_a\beta_c/(\beta_a+\beta_c)$. The corrosion current density $I_{corr}$ is substituted in equation (1): $V=(M/Z.F)$. So that, the corrosion rate V of the test piece 2 is finally calculated.

The measuring apparatus shown in FIG. 1 is a three-electrode type having a test piece 2 (working electrode), counter electrode 6 and reference electrode 8. This three-electrode type apparatus may be replaced by a two-electrode type such as illustrated in FIG. 5.

Figure 5:
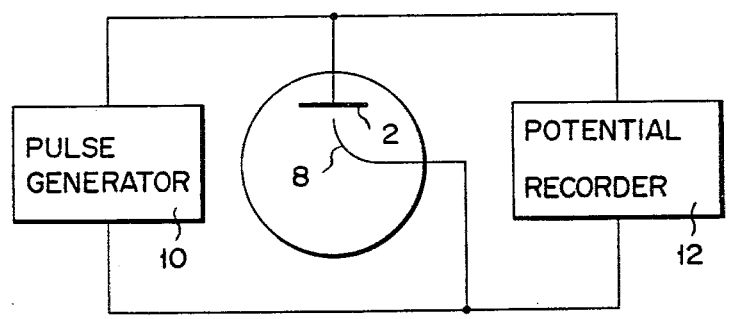
FIG. 5 is a block diagram of a measuring apparatus of two-electrode type.

The measuring apparatus shown in FIG. 5 comprises a metal test piece (or working electrode) 2 and a reference electrode 8 which also acts as a counter electrode for supplying charge to the test piece 2. Of course, the reference electrode 8 functions to detect the polarization potential of the metal test piece 2. The reference electrode 8 should keep its potential constant during measurement. Between the test piece 2 and the reference electrode 8 a pulse generator 10 and a potential difference recorder 12 are connected as illustrated in FIG. 5.

With reference to FIGS. 6 to 11, various measuring apparatus for carrying out the method of evaluating the corrosion rate of metal according to this invention will be described more in detail.

Figure 6:
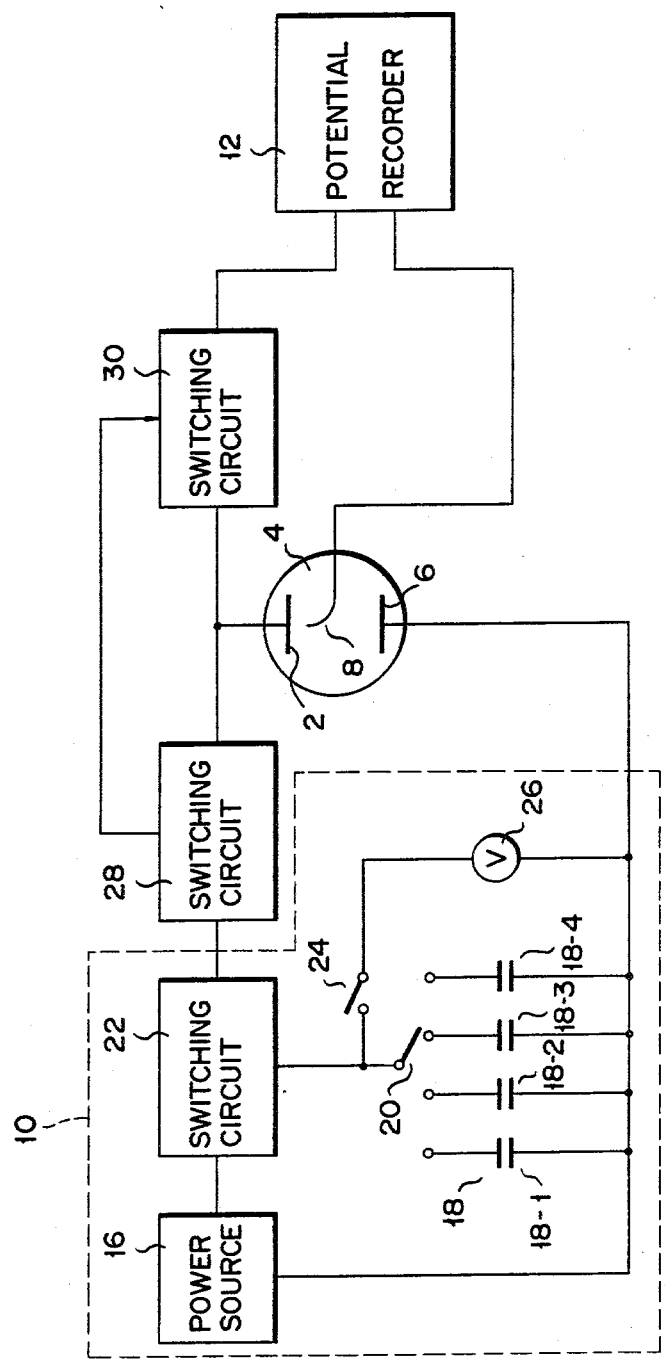
FIGS. 6 to 9 are circuit diagrams each illustrating an apparatus for carrying out the method of evaluating the corrosion rate of metal according to this invention.

The apparatus shown in FIG. 6 comprises a metal test piece 2, a cell 4 filled with a test solution, a counter electrode 6, a reference electrode 8, a pulse generator 10 and a potential difference recorder 12. The pulse generator 10 is constituted by a power source 16, four capacitors 18-1 to 18-4 for accumulating charge from the power source 16, a rotary switch 20 for selecting one of the capacitors and a first switching circuit 22 for instantaneously applying charge from the selected capacitor to the metal test piece 2. The capacitors 18-1 to 18-4 have different capacitances $C_1$ to $C_4$, respectively. One end of each capacitor is connected to the corresponding fixed contact of the rotary switch 20, and the other end to the power source 16 and the counter electrode 6. The movable contact of the rotary switch 20 is connected to the power source 16 through the first switching circuit 22.

The capacitors 18-1 to 18-4 and the rotary switch 20 constitute a series circuit. The pulse generator 10 is provided with a switch 24 and a voltmeter 26 which is connected in series. This series circuit is connected in parallel to the series circuit of the capacitors 18-1 to 18-4 and the rotary switch 20. The voltmeter 26 detects any potential change of the selected capacitor. Based on the detected potential change and the capacitance of the selected capacitor, the charge q applied to the test piece 2 is calculated.

double layer of the test piece 2. Upon a lapse of time which is determined by the resistance of resistor 58 and capacitance of the capacitor 56, relay 54 is energized to open its normally closed contact. At the same time, relay 62 is energized to have its movable contact brought into contact with its first fixed contact. As a result, charge supply to the test piece 2 is stopped, and the potential difference recorder 12 starts recording the decay of the polarization potential $\eta_t$ of the test piece 2. The recorded decay of the potential $\eta_t$ is analyzed in the aforementioned way, thereby to obtain a polarization resistance $R_p$, anodic Tafel slope $\beta_a$ or cathodic Tafel slope $\beta_c$.

Figure 8:
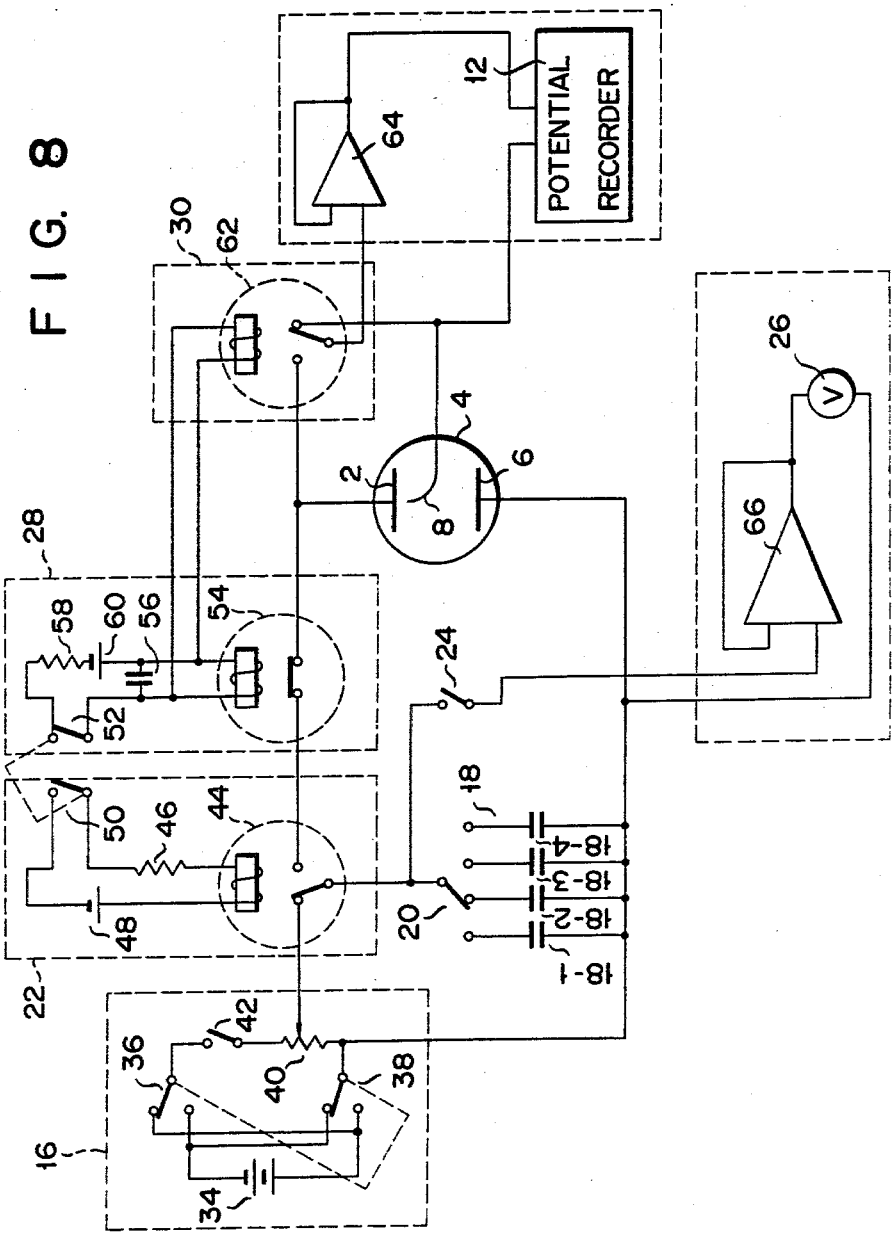
Figure 9:
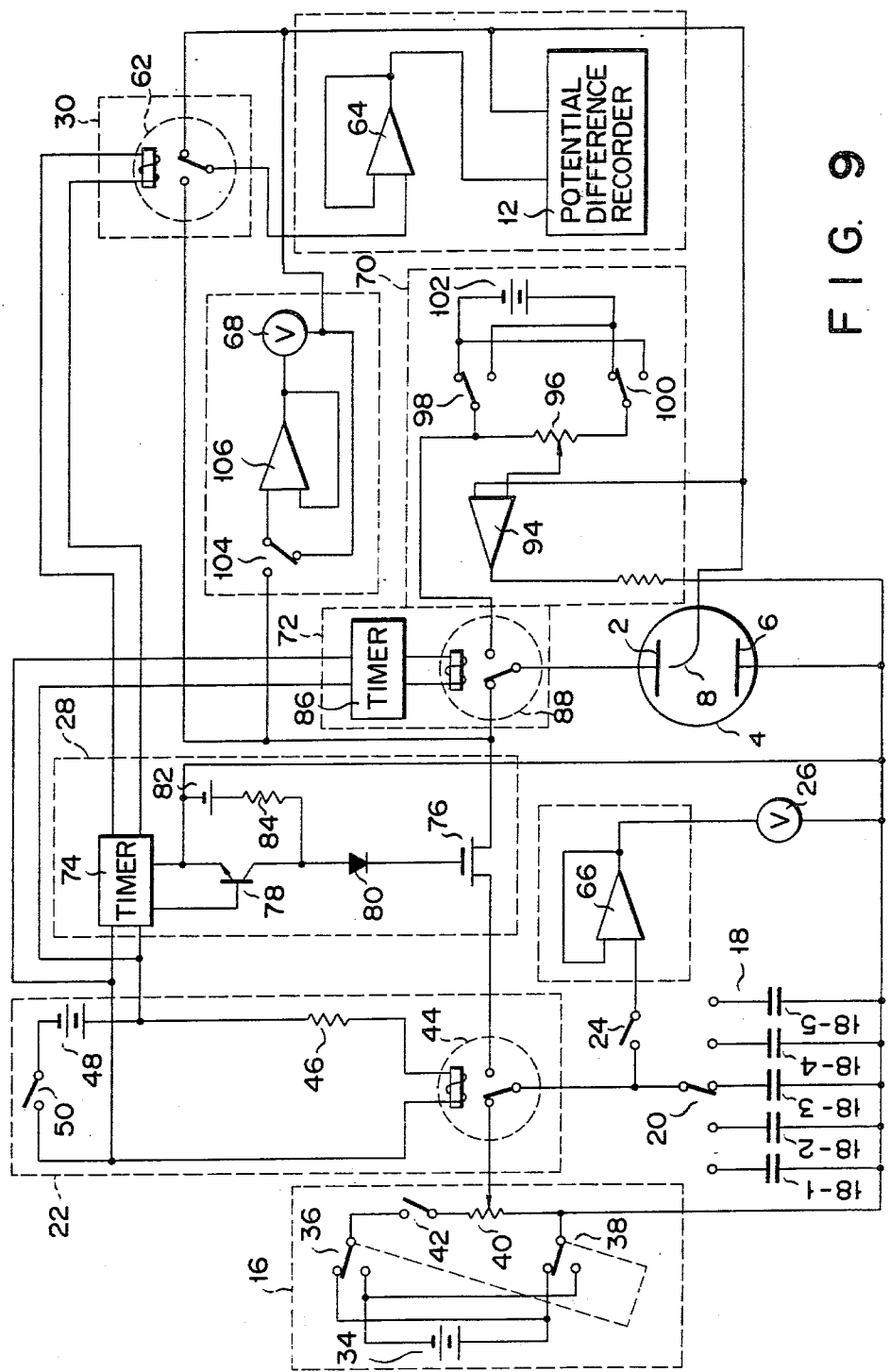

The measuring apparatus of FIG. 8 may be modified as shown in FIG. 9. The modified apparatus differs in that it is provided with a voltmeter 68 and a bias circuit 70 and its second switching circuit 28 is somewhat different. Voltmeter 68 is provided to detect the corrosion potential $E_{corr}$ of the test piece 2, and the bias circuit 70 is provided to apply a bias voltage on the test piece 2 to forcibly bring the potential thereof back to the corrosion potential $E_{corr}$ upon completion of recording of a polarization variation. The apparatus shown in FIG. 9 is further provided with a fourth switching circuit 72 for connecting the test piece 2 to the bias circuit 70.

The second switching circuit 28 of the apparatus of FIG. 9 includes a timer 74 and a FET (field effect transistor) 76. The timer is connected to a series circuit constituted by starting switch 50 and battery 48. The FET 76 has its source and drain connected to the second fixed contact of relay 44 and the fourth switching circuit 72, respectively. One output of the timer 74 is connected to the base and emitter of transistor 78, the collector of which is connected to the gate of the FET 76 through diode 80. Between the emitter and collector of the transistor 78, battery 82 and resistor 84 are connected to form a series circuit. The emitter of the transistor 78 is connected to the counter electrode 6.

The fourth switching circuit 72 is constituted by a timer 86 and a relay 88. The timer 86 is connected in parallel to the series circuit of starting switch 50 and battery 48. The relay 88 is connected to the output of the timer 86. The relay 88 has a first fixed contact connected to the drain of FET 76, a second fixed contact connected to the bias circuit 70 and a movable contact connected to the test piece 2. The movable contact of the relay 88 is kept connected to the first fixed contact so long as the relay 88 is not energized.

The output of the timer 74 of the second switching circuit 28 is connected to the relay 62 of third switching circuit 30. The bias circuit 70 is constituted by operational amplifier 94, variable resistor 96, a pair of polarity changeover switches 98 and 100 and a battery 102. The operational amplifier 94 acts as a voltage restricting circuit and has its output connected to the counter electrode 6 through a resistor 95. One input terminal of the operational amplifier 94 is connected to the reference electrode 8. Variable resistor 96 has its movable contact connected to the other input terminal of the operational amplifier 94. Battery 102 is connected between the polarity changeover switches 98 and 100. The potential applied to the test piece 2 by the bias circuit 70 is the difference between the polarization potential of the test piece 2 and the corrosion potential $E_{corr}$ detected by the voltmeter 68. This potential is controlled by the variable resistor 96. Voltmeter 68 is connected between the reference electrode 8 and the first fixed contact of the relay 88 of the fourth switching circuit 72, through operational amplifier 106 and switch 104.

The movable contact of switch 104 is connected to the input terminal of the operational amplifier, one of the fixed contacts of switch 104 is connected to the voltmeter and the other fixed contact is connected to the first fixed contact of relay 88.

It will now be described how the measuring apparatus shown in FIG. 10 operates. First, switch 104 is changed over, whereby the natural potential $E_{corr}$ of the metal test piece 2 is measured by the voltmeter 68. Then, the variable resistor 96 of the bias circuit 70 is adjusted so that its movable contact may receive the same potential as the natural potential $E_{corr}$ of the test piece 2. When the start switch 50 is closed, the relay 44 of the first switching circuit 22 is energized to bring the movable contact of the relay 44 into contact with the second fixed contact. At the same time the timer 74 is operated to turn on the transistor 78. As a result, conduction is effected between the source and drain of the FET 76, and the selected capacitor starts applying charge to the test piece 2. Upon lapse of a predetermined time, for example several microseconds to tens of milliseconds, the timer 74 turns off the transistor 74, whereby conduction between the source and drain of the FET 76 is no longer achieved and the relay 62 is energized. When the supply of charge to the test piece 2 is stopped, the movable contact of the relay 62 to the third switching circuit 30 is put into contact with the first fixed contact of the relay 62. Then, the potential recorder 12 starts recording the variation of the polarization potential $\eta_t$. Upon lapse of a predetermined time the timer 86 energizes the relay 88, thereby bringing the movable contact thereof into contact with the second fixed contact thereof. Consequently, the bias circuit 70 applies a prescribed potential on the test piece 2, thus bringing the test piece 2 back to the corrosion potential $E_{corr}$. Namely, the potential of the test piece 2 detected by the reference electrode 8 is compared with the same potential as the natural potential $E_{corr}$ appearing at the movable contact of the variable resistor 96, and the voltage corresponding to the potential difference is applied between the counter electrode 6 and the test piece 2 by the operational amplifier 94. As a result, a charge exchange is effected between the test piece 2 and the counter electrode 6, whereby the potential of the test piece 2 is brought back to the natural potential $E_{corr}$. After the potential of the test piece 2 has been brought to the corrosion potential $E_{corr}$, a variation of the polarization potential $\eta_t$ of the test piece 2 can be recorded again.

With reference to FIGS. 10A, 10B and 11, measuring apparatus including a data analyzing device for carrying out the method of evaluating the corrosion rate of metal according to this invention will be described.

The apparatus shown in FIGS. 10A, 10B comprises a power source section 110, a voltage comparator section 112, a $\eta_t$-t data generating section 114, a data processing section 116 and a control section 118. The power source section 110 charges capacitor 18 to a prescribed voltage. The voltage comparator section 112 detects the voltage applied to the capacitor 18 and gnerates a signal which stops the charge supply from the capacitor 18 to a metal test piece 2. The $\eta_t$-t data generating section 114 detects the decay of the polarization potential $\eta_t$ of the test piece 2 and generates data on the decay time of the polarization potential $\eta_t$. The data processing section 116 analyzes the data from the $\eta_t$-t data generating The first switching circuit 22 connects the selected capacitor to the power source 16 so that the capacitor is charged. It connects any one of capacitors 18-1 to 18-4 between the metal test piece 2 and the counter electrode 6 so that the electrical double layer of the test piece 2 is charged. As will be described later, the first switching circuit 22 is constituted by a timer and a relay.

The measuring apparatus of FIG. 6 further comprises a second switching circuit 28 and a third switching circuit 30. The second switching circuit 28 is connected between the metal test piece 2 and the first switching circuit 22. The second switching circuit 28 disconnects the test piece 2 from the first switching circuit 22 upon completion of the necessary charge supply from the selected capacitor to the test piece 2 through the first switching circuit 22. Thus, the second switching circuit 28 is provided for detecting an accurate polarization potential of the metal test piece 2. That is, without the circuit 28, the selected capacitor would keep applying charge to the test piece 2 even while the recorder 12 is detecting the polarization potential of the test piece 2. As result, the recorder 12 would unnecessarily detect an ohmic drop. If the detected potential of the test piece 2 contains an ohmic drop, it is impossible to obtain a correct $\eta_t$-t curve.

In other words, the second switching circuit 28 opens upon lapse of a specific period of time from the start of charge supply to the test piece 2, thereby stopping the charge supply. Thus, the reference electrode 8 can detect exclusively the varying potential $\eta_t$ of the test piece 2, never an ohmic drop after the circuit 28 has opened. Consequently, a correct $\eta_t$-t curve containing no error due to the solution resistance $R_s$ etc. is obtained. Said specific period is such a time within which the test piece 2 can be charged to have predetermined polarization potential $\eta_n$ which is within 30 to $-30$ millivolts, preferably 10 to $-10$ millivolts in order to obtain the polarization resistance $R_p$, which is 30 millivolts or more, preferably 50 millivolts or more in order to obtain Tafel slope $\beta_a$, and which is $-30$ millivolts or lower, preferably $-50$ millivolts or lower in order to obtain Tafel slope $\beta_c$. If the solution resistance $R_s$ is not large the second switching circuit 28 is unnecessary.

The third switching circuit 30 is connected between the test piece 2 and the potential difference recorder 12 and is operated whenever the second switching circuit 28 disconnects the test piece 2 from the first switching circuit 22. When operated, the circuit 30 prevents high voltage from being applied abruptly on the potential difference recorder 12. It operates substantially at the same time together with the second switching circuit 28 so as to connect the recorder 12 to the test piece 2 only for a period of time during which the recorder 12 is to detect the polarization potential of the test piece 2.

Figure 7:
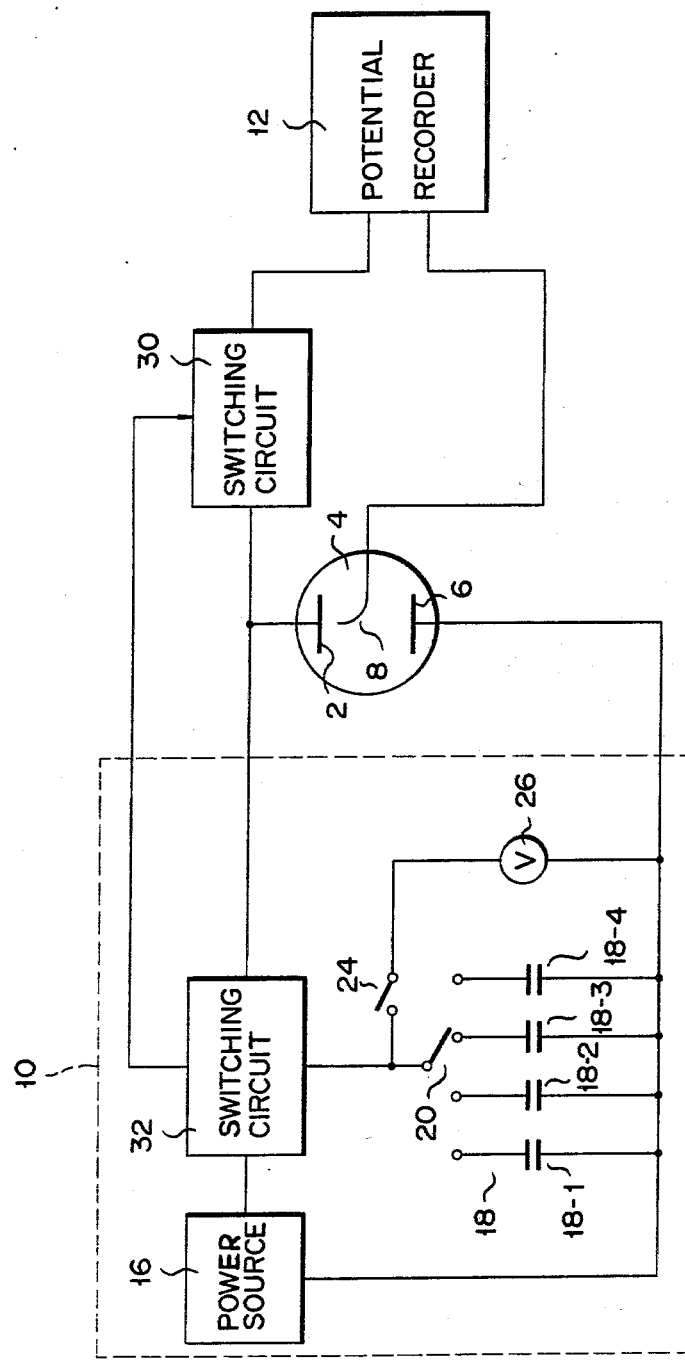

The measuring apparatus shown in FIG. 7 differs from the apparatus of FIG. 6 only in that a single switching circuit 32 is provided in place of the first switching circuit 22 and the second switching circuit 28. The switching circuit 32 connects the selected capacitor to the power source 16 so that the capacitor is charged. It connects the selected capacitor between the test piece 2 and the counter electrode 6 so that the charge is applied from the capacitor to the test piece 2. It disconnects the selected capacitor from the test piece 2 while the polarization potential of the test piece 2 is detected.

The measuring apparatus shown in FIG. 6 is more fully illustrated in FIG. 8. As shown in FIG. 8, the power source 16 is constituted by a battery 34, a pair of polarity changeover switches 36 and 38 ganged to each other, a variable resistor 40 and a switch 42. The variable resistor 40 and the switch 42 form a series circuit, which is connected between the movable contacts of the polarity changeover switches 36 and 38. The polarity changeover switches 36 and 38 are so connected to the battery 34 as to apply a positive charge or a negative charge to the test piece 2, thereby obtaining Tafel slope $\beta_a$ of the anodic reaction of the test piece 2 and Tafel slope $\beta_c$ of cathodic reaction of the test piece 2 and also obtaining polarization resistance $R_p$ if necessary. The variable resistor 40 is provided to control the voltage applied to the selected capacitor.

The first switching circuit 22 is constituted by a relay 44, a resistor 46, a battery 48 and a starting switch 50 for energizing the relay 44. The relay 44 has a first fixed contact connected to the movable contact of the variable resistor 40, a second fixed contact connected to the test piece through the second switching circuit 28, and a movable contact connected to the rotary switch 20. The movable contact of the relay 44 is normally in contact with the first fixed contact and is brought into contact with the second fixed contact when the relay 44 is energized.

The second switching circuit 28 is constituted by a relay 54, a starting switch 52 connected to the relay 54, a capacitor 56 connected in parallel to series connected starting switch 52, a resistor 58, and a battery 60. The relay 54 has a normally closed contact connected between the test piece 2 and the second fixed contact of the relay 44. The start switch 52 is ganged with the start switch 50 of the first switching circuit 22.

The third switching circuit 30, which is connected between the test piece 2 and the potential difference recorder 12, is constituted by a relay 62 which is connected in parallel to the capacitor 56 of the second switching circuit 28. The relay 62 has a first fixed contact connected to the test piece 2, a movable contact and a second fixed contact connected to the reference electrode 8. The potential difference recorder 12 is provided with an operational amplifier 64 which acts as a voltage follower. The movable contact of the relay 62 is connected to the operational amplifier 64 and is normally in contact with the second fixed contact and is put into contact with the first fixed contact when the relay 62 is energized. The operational amplifier 64 is connected to the recorder 12. Another operational amplifier 66 is connected between the voltmeter 26 and the switch 24.

It will now be described how the measuring apparatus shown in FIG. 8 operates. First, rotary switch 20 is operated to select one of the capacitors 18-1 to 18-4. Which capacitor is selected depends on which is to be obtained, the polarization resistance $R_p$ of the test piece 2, Tafel slope $\beta_a$ of anodic reaction, or Tafel slope $\beta_c$ of cathodic reaction. The selection of capacitor also depends on the material and the surface area S of the test piece 2 and the properties of the test solution. Then, the polarity changeover switches 36 and 38 are set to apply a positive or negative charge to the test piece 2. This done, the movable contact of the variable resistor 40 is so moved as to apply a specific voltage on the selected capacitor. Thereafter the switch 42 is closed thereby to charge the selected capacitor. Switch 24 is then closed so that the voltmeter 26 measures the voltage applied to the selected capacitor. Then, both start switches 50 and 52 are closed to start supplying charge to the electrical section 114 to obtain a corrosion current density $I_{corr}$ or a corrosion rate V. The control section 118 generates a mode signal according to a measuring mode.

Between the test piece 2 and the power source section 110 there are connected starting switch unit 120, first switch unit 122 and second switch unit 124. The starting switch unit 120 makes it possible to apply voltage from the power source section 110 to the test piece 2. The first switch unit 122 connects the capacitor 18 to either the power source section 110 or the test piece 2. The second switch unit 124 stops the voltage supply to the test piece 2.

The power source section 110 is constituted by registers 126, 128 and 130 storing digital voltage values $V_1$, $V_2$ and $V_3$ to be applied to the capacitor, a selector 132 connected to the registers 126 to 130 for selecting one of the them according to a measuring mode signal from the control section 118, and a digital-analog converter 134 provided with a power source for converting a digital voltage value $V_1$ from the selector 132 into an analog value thereby to supply a predetermined voltage $V_1$ to the test piece 2. The voltage comparator section 112 is constituted by an analog-digital converter 136, a comparator 128 connected to the analog-digital converter 136, a measuring mode selector 140 connected to the comparator 138, registers 142, 144 and 146 storing digital voltage values $V_{c1}$, $V_{c2}$ and $V_{c3}$ and connected to the measuring mode selector 140, and a flip-flop 148. The analog-digital converter 136 is connected to the capacitor 18 for converting the voltage on the capacitor into a digital value. The comparator 138 compares a set value from the selector 140 with a detected voltage value from the capacitor. Like the selector 132 of the power source section 110, the selector 140 selects one of the registers 142 to 146 according to a measuring mode signal from the control section 118. The comparator is connected to the reset terminal of the flip-flop 148, the output terminal of which is connected to the second switch unit 124.

The $\eta_t$-t data generating section 114 comprises an analog-digital converter 150 connected between the test piece 2 and reference electrode 8 for converting the polarization potential $\eta_t$ of the test piece 2 into a digital value. If further comprises comparators 152, 154 and 156 connected to the analog-digital converter 150. The comparators 152, 154 and 156 are connected also to selectors 158, 160 and 162, respectively. The selectors 158, 160 and 162 are connected to the control section 118 to receive a measuring mode signal therefrom. The selector 158 is connected to registers 164, 166 and 168 which store digital potential values $\eta_{11}$, $\eta_{12}$ and $\eta_{13}$, respectively. The selector 160 is connected to registers 170, 172 and 174 which store digital potential values $\eta_{21}$, $\eta_{22}$ and $\eta_{23}$, respectively. The selector 162 is connected to registers 176, 178 and 180 which store digital potential values $\eta_{31}$, $\eta_{32}$ and $\eta_{33}$, respectively. The digital potential values $\eta_{11}$ to $\eta_{13}$, $\eta_{21}$ to $\eta_{23}$ and $\eta_{31}$ to $\eta_{33}$ are present in the following relationship:

$$\eta_{11}-\eta_{21}=\eta_{21}-\eta_{31}=\Delta\eta_1$$

$$\eta_{12}-\eta_{22}=\eta_{22}-\eta_{32}=\Delta\eta_2$$

$$\eta_{13}-\eta_{23}=\eta_{23}-\eta_{33}=\Delta\eta_3$$

The $\eta_t$-t data generating section 114 further comprises a clock pulse generator 182, an AND gate 184, three counters 186, 188 and 190 and three registers 192, 194 and 196. The clock pulse generator 182 is connected through the AND gate 184 to the counters 186, 188 and 190 for counting clock pulses. The counter 186 is connected to the comparator 152 and the register 192 for latching the count of the counter 186. The counter 188 is connected to the comparator 154 and the register 194 for latching the count of the counter 188. The counter 190 is connected to the comparator 156 and the register 196 for latching the count of the counter 190.

The control section 118 is constituted by a mode counter 198, three flip-flops 200, 202 and 204, two delay circuits 206 and 208 and an AND gate 210. The mode counter 198 is connected to the comparator 156, thereby to designate a measuring mode. One output of the mode counter 198 is connected to selectors 132, 140, 152, 160 and 162 through line 212, and the other output is connected to the data processing section 116 through line 214. The mode counter 198 is connected to the data processing section 116 through line 216.

The mode counter 198 produces a measuring mode signal which is a two-bit binary code. If it is a "00" code, the measuring mode signal defines a first measuring mode for obtaining polarization resistance $R_p$. If it is an "01" code, it defines a second measuring mode for obtaining Tafel slope $\beta_a$ of anodic reaction. If it is "10" code, it defines a third measuring mode for obtaining Tafel slope $\beta_c$ of cathodic reaction. If it is an "11" code, it defines a calculation mode for operating the data processing section 116.

The control section 118 is provided with an OR gate 218. The inputs of the OR gate 218 are connected to the data processing section 116 through line 216 and to the comparator 156, respectively. The output of the OR gate 218 is connected to the set terminal of the flip-flop 200 and the reset terminal of the flip-flop 204. The delay circuit 206 is connected to the comparator 156 and to the data processing section 116 through line 220. The reset terminals of the flip-flop 200 and 202 are connected to the comparator 138 and the reset terminal of the flip-flop 148 through line 222. The output terminal of the flip-flop 200 is connected to the delay circuit 208 and to the start switch unit 120 via line 224. The delay circuit 208 is connected to the set terminal of the flip-flop 202. The delay circuit 208 has a delay time $\eta_1$ which is long enough to charge up the capacitor 18. The output terminal of the flip-flop 202 is connected to the set terminal of the flip-flop 204 and to the first switch unit 122 via a line 226. The output terminal of the flip-flop 204 is connected to one input terminal of the AND gate 184 through line 228. The output terminal of the AND gate 210 is connected to the reset terminal of the flip-flop 200 through line 230.

As illustrated in FIG. 11, the data processing section 116 is constituted by an input device 230, a data buffer 232, a data buffer controller 234, an encoder 236, an address counter 238, a memory 240, an instruction register 242, an arithmetic and logic unit 244 (herein after called "ALU"), an address controller 246 and an output device 248. The input device 230 has a keyboard and supplies a start signal to the control section 118. In response to a ready signal the input device 230 starts the data processing. Further, the input device 230 can feed data other than those detected by the data generating section 114, such as the surface area S of the metal test piece 2. The data buffer 232 temporarily stores the data from the control section 118 and input device. The data buffer controller 234 stores the data in the data buffer 232 in response to a write signal from the control section 188. The encoder 236 is connected to the input device 230 and to the address counter 238 which receives a start address signal from the encoder 236. Memory 240 is connected between the encoder 236 and the address counter 238. Memory 240 contains a previously stored micro program. The memory 240 is connected to the instruction register 242 which receives a micro instruction which is read out from the memory 240 when the address counter 238 is accessed to the memory 240. This register 242 is connected to the data buffer controller 234, the ALU 244 and the address controller 246. Thus, the operation code field (OP), source & destination code field (D) and next address field (N) of a micro instruction are supplied to the ALU 244 the data buffer controller 234, and the address controller 246, respectively. The address controller 246 is connected to the address counter 238 for increasing the address of the address counter 238 according to the next address field (N). The ALU 244 receives data from the data buffer 232 and effects an arithmetic operation on the data according to the operation code field (OP). The results of the arithmetic operation are supplied to the output device 248 and the data buffer 232. The output device 248 is constituted by, for example, an LED (light emitting device) display circuit, a cathode ray tube or a line printer.

It will now be described how the apparatus shown in 10A, 10B and 12 operates.

First, the input device 230 is operated to store in the data buffer 232 the surface area S of the test piece 2, the atomic weight M of the test piece 2 and the valence of the dissolved metal ion. Further, the input device 230 is operated to store in the data buffer 232 the voltage values, $V_1$, $V_2$ and $V_3$ and potential values $\eta_{11}$, $\eta_{12}$, $\eta_{13}$, $\eta_{21}$, $\Theta_{22}$, $\eta_{23}$, $\eta_{31}$, $\eta_{32}$ and $\eta_{33}$. At the same time, the voltage values $V_1$, $V_2$ and $V_3$ are set at the registers 126, 128 and 130, respectively, and the potential values $\eta_{11}$, $\eta_{12}$, $\eta_{13}$, $\eta_{21}$, $\eta_{22}$, $\eta_{23}$, $\eta_{31}$, $\eta_{32}$ and $\eta_{33}$ are set at the registers 164, 166, 168, 170, 172, 174 176, 178 and 180, respectively. (In FIGS. 11A, 11B and 12, the lines connecting the input device 230 to the registers are not shown.)

Then, the start key switch (not shown) of the input device 230 is depressed ($t = t_0$) to generate such a start signal as shown in FIG. 12A. The start signal is supplied to the counters 186, 188 and 190 and registers 192, 194 and 196 of the $\eta_t$-t data generating section 114, thereby clearing these counters and registers. Simultaneously, the start signal is supplied to the mode counter 198 of the control section 118 through the line 216. In response to the start signal the mode counter 198 is set at a count "00" and produces a measuring mode signal "00". The measuring mode signal "00" is supplied via line 212 to the selectors 132, 140, 158, 160 and 162. In response to the signal "00" each of these selectors selects the register which corresponds to the first measuring mode for obtaining polarization resistance $R_p$. That is, the selector 132 selects the register 126 storing the voltage value $V_1$, the selector 140, the register 142 storing the voltage value $V_{cl}$, the selector 158 the register storing the potential value $\eta_{11}$, the selector 160 the register 170 storing the potential value $\eta_{21}$, and the selector 162 the register 176 storing the potential value $\eta_{31}$.

The start signal is supplied through the OR gate 218 to the flip-flop 200, thereby setting the flip-flop 200 as illustrated in FIG. 12B. As a result, the flip-flop 200 produces an output signal "1", which is supplied to the delay circuit 208 and to the switch unit 120 via the line 224. The output signal "1" of the flip-flop 200 closes the switch unit 120, whereby a voltage $V_1$ corresponding to the value $V_1$ stored in the register 126 is applied from the digital-analog converter 134 to the capacitor 18. Thus, charge supply to the capacitor 18 is started, and at the same time the delay circuit 208 starts working. Upon lapse of time $t_1$ which is determined by the delay time $\tau_1$ of the delay circuit 208, the delay circuit 208 generates an output signal, which is supplied to the flip-flop 202. In response to the output signal of the delay circuit 208, the flip-flop 202 produces an output signal "1" such as illustrated in FIG. 12C ($t = t_1$). The output signal "1" of the flip-flop 202 is supplied to the flip-flop 148 through the line 226. Upon receipt of this signal the flip-flop 148 is set and produces an output signal. The output signal of the flip-flop 148 is supplied to the second switch unit 124. As a result, the second switch unit 124, which is normally opened, is closed.

When the second switch unit 124 is closed, the first switch unit 122 is operated so as to connect the capacitor 18 to the test piece 2. Consequently, the charge accumulated in the capacitor 18 is supplied to the test piece 2 through the closed second switch unit 124. At the same time the output signal "1" of the flip-flop 202 sets the flip-flop 204, which produces an output signal "1". The output signal of the flip-flop 204 is supplied to the AND gate 184 through line 228. As a result, the AND gate 184 is opened, whereby clock pulses are supplied from the clock pulse generator 182 to the counters 186, 188 and 190. These counters therefore start counting clock pulses upon lapse of time $t_1$ from $t_0$. At $t_1$ the measuring apparatus starts recording the polarization potential $\eta_t$ of the test piece 2.

When connected to the test piece 2 by the first switch unit 122, the capacitor 18 has its voltage lowered abruptly. The voltage of the capacitor 18 is applied to the comparator 138 through the analog-digital converter 136 and is compared with the voltage value $V_{cl}$ stored in the register 142 which has been selected by the selector 140. When the voltage of the capacitor 18 becomes equal to the voltage value $V_{cl}$, the comparator 138 generates an output signal, which is supplied to the reset terminal of the flip-flop 148 and which resets the flip-flop 148 which has been set by the output signal of the flip-flop 202. As a result, the second switch unit 124 is opened, and the charge is no longer applied to the test piece 2 from the capacitor 18. The output signal of the comparator 18 is also supplied to the reset terminals of the flip-flops 200 and 202 via line 222, thereby resetting both flip-flops 200 and 202. When the flip-flops 200 and 202 are reset, the start switch unit 120 is opened and the first switch unit 122 is operated so as to be connected to the start switch unit 120.

As clearly understood from the above description, the charge q applied to the double layer of the test piece 2 is expressed as the product of the capacitance $C_{18}$ of the capacitor 18 and the difference between the voltage value $V_1$ stored in the register 126 and the voltage value $V_{cl}$ stored in the register 142. That is:

$$q = (V_1 - V_{cl}) \times C_{18}.$$

All these values $V_1$, $V_{cl}$ and $C_{18}$ are stored in the data buffer 232 as mentioned above.

As illustrated by curve 250 in FIG. 13, the polarization potential of the test piece 2 starts decaying at $t_1$, due to a corrosion reaction. The varying polarization potential $\eta_t$ is detected by the reference electrode 4, converted into a digital value by the analog-digital converter 150, and supplied to the comparators 152, 154 and 156. The comparator 152 compares this digital value with the potential value $\eta_{11}$ stored in the register 164 which has been selected by the selector 158. When the the digital data from the converter 150 becomes equal to the potential value $\eta_{11}$ (t=t$_3$), the comparator 152 generates an output signal. The output signal of the comparator 152 stops the counter 186 as illustrated in FIG. 12E. The count $N_{11}$ at this moment indicates time $T_{11}$ (=t$_3$-t$_1$). In a similar way, when the polarization potential $\eta_t$ drops to the potential value $\eta_{21}$ stored in the register 170 (t=t$_4$), the comparator 154 generates an output signal to stop the counter 188. The counter $N_{21}$ of the counter 188 indicates time $T_{21}$ (=t$_4$-t$_1$). Further, when the polarization potential $\eta_t$ drops to the potential value $\eta_{31}$ stored in the register 176 (t=t$_5$), the comparator 156 produces an output signal to stop the counter 190. The count $N_{31}$ of the counter 190 represents time $T_{31}$ (=t$_5$-t$_1$). The output signal of the comparator 156 is supplied also to the mode counter 198.

In response to the signal from the comparator 156 the mode counter 198 functions to have its count changed from "00" to "01" and thus produces a measuring mode signal "01" which defines the second measuring mode for obtaining Tafel slop $\beta_a$ of anodic reaction. The measuring mode signal "01" is supplied via line 212 to selectors 132, 140, 158, 160 and 162. The output signal of the comparator 156 is supplied via the OR gate 218 to the set terminal of the flip-flop 200 and the reset terminal of the flip-flop 204. Thus, the flip-flop 200 is set, and the flip-flop 204 is reset. As a result, the start switch unit 120 is closed to apply voltage $V_2$ to the capacitor 18, and the AND gate 184 is opened to stop supplying clock pulses from the clock pulse generator 182 to the counters 186, 188 and 190. The output signal of the comparator 156 is supplied also to the delay circuit 206 (t=t$_5$). The delay circuit has a delay time $\tau_2$. Upon lapse of $\tau_2$, the delay circuit 206 generates an output signal, which is supplied to the counters 186, 188 and 190. When the leading edge of the output signal of the delay circuit 206 reaches the counters 186, 188 and 190, the counts $N_{11}$, $N_{21}$ and $N_{31}$ of these counters are latched by the registers 192, 194 and 196, respectively. The output signal of the delay circuit 206 is supplied via line 220 as a write signal to the data buffer controller 234 of the data processing section 116. The controller 234 gives a write instruction to the data buffer 232. Specified ones of the registers of the buffer 232 start storing the counts $N_{11}$, $N_{21}$ and $N_{31}$, i.e. the contents of the registers 192, 194 and 196. Upon completion of this data storage, the trailing edge of the output signal of the delay circuit 206 reaches the counters 186, 188 and 190, whereby the counters 186, 188 and 190 and the registers 192, 194 and 196 are cleared.

As described in the preceding paragraph, the second measuring mode is started when the flip-flop 200 is set and the mode counter 198 receives an output signal of the comparator 156 to have its count changed to "01". The second measuring mode is carried out in substantially the same way as in the first measuring mode. The selector 132 selects the register 128 storing the voltage value $V_2$, the selector 158 the register 166 storing the potential value $\eta_{12}$, the selector 160 the register 172 storing the potential value $\eta_{22}$, the selector 162 the register 178 storing the potential value $\eta_{32}$, and the selector 140 the register 144 storing the voltage value $V_{c2}$. The polarization potential $\eta_t$ of the test piece 2 decays as illustrated by a curve 252 in FIG. 13. As shown in FIGS. 13 and 14, the counter 186 counts clock pulses until its count reaches $N_{12}$ which indicates a time $T_{12}$, the counter 188 counts clock pulses until its count reaches $N_{22}$ which indicates a time $T_{22}$, and the counter 190 counts clock pulses until its count reaches $N_{23}$ which indicates a time $T_{23}$. The counts $N_{12}$, $N_{22}$ and $N_{32}$ are written into the data buffer 232.

The third measuring mode is started when the flip-flop 200 is set and the mode counter 198 receives an output signal of the comparator 156 to have its count changed to "10". It is carried out in substantially the same way as are the first and second measuring modes. The selector 132 selects the register 130 storing the voltage value $V_3$, the selector 138 the register 146 storing the voltage value $V_{c3}$, the selector 158 the register 168 storing the potential value $\eta_{13}$, the selector 160 the register 174 storing the potential value $\eta_{23}$, and the selector 162 the register 176 storing the potential $\eta_{33}$. The polarization potential $\eta_t$ of the test piece 2 increases with time as illustrated by curve 254 in FIG. 13. As shown in FIGS. 12 and 13, the counter 186 counts clock pulses until its count reaches $N_{13}$ which indicates a time $T_{13}$, the counter 188 counts clock pulses until its count reaches $N_{23}$ which indicates a time $T_{23}$, and the counter 190 counts clock pulses until its count reaches $N_{33}$ which indicates a time $T_{33}$. These counts $N_{13}$, $N_{23}$ and $N_{33}$ are written into the data buffer 232. The second measuring mode is completed when the comparator 156 generates an output signal.

Upon receipt of the output of the comparator 156, the mode counter 198 functions to have its count changed to "11" which represents the calculation mode. Then, the mode counter 198 supplies a ready signal to the input device 230 through the AND gate 210 and line 214. A "ready" lamp (not shown) of the keyboard of the input device 230 is lit in response to the ready signal. The operator sees the "ready" lamp lit up and then depresses a calculation mode designating key (not shown). Then, a start address signal is supplied to the address counter 238. Suppose the 100th address of the memory 240 stores a start micro instruction of the micro program for calculating a corrosion current density $I_{corr}$. Then, the start address signal is supplied to the memory 240 from the address counter 238, whereby the start micro instruction is supplied from the 100th address to the instruction register 242. The operation code field (OP), source & destination code field (D) and next address field (N) of the micro instruction are supplied to the ALU 244, the data buffer controller 234 and the address controller 246, respectively. Then the ALU 244 reads the data from the data buffer 232 and effects an arithmetic operation on the data according to the operation code (OP). The results of the arithmetic operation are stored into one of the registers of the data buffer 232 which as been selected by the source 8 destination code field (D) supplied to the data buffer controller 234. In accordance with next address field (N) the address controller 246 determines the number of the address to be set in the address counter 238. The ALU 244 carries out similar arithmetic operations until the corrosion current density $I_{corr}$ is obtained. The obtained value of $I_{corr}$ is supplied to the output device 248, which displays the value of $I_{corr}$.

In order to obtain the corrosion rate V of the test piece 2, the operator depresses a corrosion rate calculation key (not shown) of the input device 230. Then, an address designating signal is supplied to the address counter 238 and to the memory 240. In response to the address designating signal the memory 230 supplies the instruction register 242 with the starting micro instruction of the micro program for calculating a corrosion rate V. The operation code field (OP), source & destination code field (D) and next address field (N) of the start micro instruction are supplied to the ALU 244, the data buffer controller 234 and the address controller 246, respectively. Then the ALU 244 reads necessary data from the memory 240 and the value of $I_{corr}$ from one of the registers of the data buffer 232. The ALU 244 carries out an arithmetric operation on these data according to the operation code (OP) of the micro instruction, thereby calculating the corrosion rate V. The value of the corrosion rate V is supplied to the output device 248 and is displayed.

The polarization resistance $R_p$, Tafel slope $\beta_a$ of anodic reaction and Tafel slope $\beta_c$ of cathodic reaction can be obtained one by one merely by depressing the key of the input device 230 to designate the address of the memory which stores the starting micro instruction of a micro program for calculating $R_p$, $\beta_a$ or $\beta_c$.

The method and measuring apparatus for evaluation of the corrosion rate of metal according to this invention can obtain a corrosion rate V, which is very similar to that obtained by the weight loss method.

Namely, when a plate of soft steel SB46 was used as the metal test piece 2 and immersed in city water filled in the cell 4, the corrosion (natural) potential of the plate was detected to be $-0.655V_{vs}.SCE$. Then, a charge of 0.06 μc was instantaneously applied to the plate through the counter electrode 6. From the variation of the polarization $\eta_t$ of the plate the differential capacitance $C_d$ of the plate was determined to be 140 μFcm$^{-2}$. As a result, the polarization resistance $R_p$ of the metal test piece was calculated to be 2.4 KΩ.cm$^2$. The polarization potential of the test piece was then brought back to $-0.655V_{vs}.SCE$, and a charge of +3 μc was applied to the test piece instantaneously. As a result, a Tafel slope $\beta_a$ of 75 mV was obtained. Thereafter, the polarization potential of the plate was brought back to $-0.655V_{vs}.SCE$, and charge of $-3$ μc was applied to the plate. Then, a Tafel slope $\beta_c$ of 100 mV was obtained. The values thus obtained were analyzed, thereby obtaining a current density $I_{corr}$ of 8.1 A/cm$^2$. From this current density $I_{corr}$ the corrosion rate V of soft steel SB46 was calculated, considering that soft steel SB46 chiefly consists of iron. The evaluated corrosion rate V corresponds to 20 mdd.

A plate of soft steel SB46 was used in the weight loss method. The corrosion rate V' of the plate evaluated by this method turned out to be 21 mdd, which is very similar to the corrosion rate V obtained by the method and measuring apparatus according to the present invention.

As described above, this invention provides a method of evaluating the corrosion rate of metal in which the corrosion current density $I_{corr}$ of a metal test piece is correctly detected and analyzed to obtain an accurate corrosion rate V, and it also provides a measuring apparatus for carrying out the method.

What we claim is:
1. A method of evaluating the corrosion rate of metal in a corrosive solution, comprising:
(A) the step of determining the polarization resistance $R_p$ of a metal test piece having a surface area S and disposed in a corrosive solution, said step comprising:
  (i) instantaneously feeding a given charge $q_{Rp}$ to the electrical double layer of the test piece, thereby changing the potential of the test piece to have a predetermined polarization potential $n_{Rp}$;
  (ii) detecting, as a function of time, the variation of the polarization potential $n_{Rp}(t)$ of the test piece due to a corrosion reaction, using a reference electrode disposed in the corrosive solution;
  (iii) estimating an initial polarization potential $n_{Rp}(0)$ of the test piece upon completion of the charge supply (t=0), based on the polarization potential $n_{Rp}(t)$ detected as a function of time; and
  (iv) calculating the polarization resistance $R_p$ based on the given charge $q_{Rp}$, initial polarization potential $n_{Rp}(0)$, surface area S, and the slope of log $n_{Rp}(t)$-t relation;
(B) the step of determining the Tafel slope $\beta_a$ of anodic reaction of the metal test piece, said step comprising:
  (i) instantaneously feeding the electrical double layer of the test piece with a charge $q_{\beta a}$ whose absolute value is larger than that of charge $q_{Rp}$, thereby changing the potential of the test piece to have a predetermined polarization potential $n_{\beta a}$ whose value is positive and higher than the polarization potential $n_{Rp}$;
  (ii) detecting, as a function of time, the variation of the polarization potential $n_{\beta a}(t)$ of the test piece due to a corrosion reaction, using the reference electrode; and
  (iii) calculating the Tafel slope $\beta_a$ of the test piece based on the polarization potential $n_{\beta a}(t)$ of the test piece detected as a function of time,
(C) the step of determining the Tafel slope $\beta_c$ of cathodic reaction of the metal test piece, said step comprising:
  (i) instantaneously feeding the electrical double layer of the test piece with a charge $q_{\beta c}$ whose absolute value is larger than that of the charge $q_{Rp}$ and whose polarity is opposite to that of the charge $q_{\beta a}$, thereby changing the potential of the test piece to have a predetermined polarization potential $n_{\beta c}$ whose value is negative;
  (ii) detecting, as a function of time, the variation of the polarization potential $n_{\beta c}(t)$ of the test piece due to a corrosion reaction, using the reference electrode; and
  (iii) calculating the Tafel slope $\beta_c$ of the test piece based on the polarization potential $n_{\beta c}(t)$ of the test piece detected as a function of time, and
(D) the step of calculating the corrosion current density $I_{corr}$ of the metal test piece based on the polarization resistance $R_p$, anodic Tafel slope $\beta_a$ and cathodic Tafel slope $\beta_c$.

2. A method according to claim 1, in which said initial polarization potential $\eta_{Rp}(0)$ is obtained by extrapolating the variation of the polarization potential $\eta_{Rp}(t)$ as a function of time.

3. A method according to claim 1, in which said polarization resistance $R_p$ is calculated from the differential capacitance $C_d$ of the electrical double layer of the test piece which is obtained from the charge density $\Delta q = q/S$ of the charge fed to the test piece per unit area S and the initial polarization potential $\eta_{Rp}(0)$ obtained from the polarization potential variation as a function of time.

4. A method according to claim 3, in which said initial polarization potential $\eta_{Rp}(0)$, said charge density $\Delta q$ and said differential capacitance $C_d$ are related by the equation $C_d = \Delta_q/\eta_{Rp}(0)$, and said polarization resistance $R_p$ is expressed by the slope of the logarithmic function $\log \eta_{Rp}(t)$ versus time t.

5. A method according to claim 1, in which said Tafel slope $\beta_a$ of anodic reaction is obtained by sampling from the variation of the polarization potential $\eta_{\beta a}(t)$ polarization potential $\eta_{\beta a}(t_1)$, $\eta_{\beta a}(t_2)$ and $\eta_{\beta a}(t_3)$ at times $t_1$, $t_2$ and $t_3$ respectively and by using the following equation:

$$\frac{\exp(-\frac{2\cdot 3}{\beta_a}\eta_{\beta a}(t_1)) - \exp(-\frac{2\cdot 3}{\beta_a}\eta_{\beta a}(t_2))}{\exp(-\frac{2\cdot 3}{\beta_a}\eta_{\beta a}(t_2)) - \exp(-\frac{2\cdot 3}{\beta_a}\eta_{\beta a}(t_3))} = \frac{t_1 - t_2}{t_2 - t_3}$$

6. A method according to claim 5, in which said sampling of polarization potentials is carried out in such a way as to satisfy the following equation:

$$\eta_{\beta a}(t_1) - \eta_{\beta a}(t_2) = \eta_{\beta a}(t_2) - \eta_{\beta a}(t_3) = \Delta\eta_{\beta a},$$

and the Tafel slope $\beta_a$ is obtained by the following equation:

$$\beta_a = \frac{\Delta\eta_{\beta a}}{\log \frac{t_3 - t_2}{t_2 - t_1}}$$

7. A method according to claim 1, in which said Tafel slope $\beta_a$ of anodic reaction is obtained by sampling from the variation of the polarization potential $\eta_{\beta a}(t)$ obtained as a function of time such polarization potentials $\eta_{\beta a}(t_1), \eta_{\beta a}(t_2), \eta_{\beta a}(t_3), \ldots \eta_{\beta a}(t_n)$ at times $t_1, t_2, t_3, \ldots t_n$ respectively as would satisfy the following equation:

$$\eta_{\beta a}(t_1) - \eta_{\beta a}(t_2) = \eta_{\beta a}(t_2) - \eta_{\beta a}(t_3) = \ldots = \eta_{\beta a}(t_{n-1}) - \eta_{\beta a}(t_n) = \Delta\eta$$

and by using the following equation:

$$\beta_a = \Delta\eta/\log \delta$$

where $$\delta = \frac{1}{n-2}\left(\frac{t_3 - t_2}{t_2 - t_1} + \frac{t_4 - t_3}{t_3 - t_2} + \ldots + \frac{t_n - t_{n-1}}{t_{n-1} - t_{n-2}}\right).$$

8. A method according to claim 1, in which said Tafel slope $\beta_c$ of cathodic reaction is obtained by sampling from the variation of the polarization potential $\eta_{\beta c}(t)$ polarization potentials $\eta_{\beta c}(t_1)$, $\eta_{\beta c}(t_2)$ and $\eta_{\beta c}(t_3)$ at times $t_1$, $t_2$ and $t_3$ respectively and by using the following equation:

$$\frac{\exp(\frac{2\cdot 3}{\beta_c}\eta_{\beta c}(t_1)) - \exp(\frac{2\cdot 3}{\beta_c}\eta_{\beta c}(t_2))}{\exp(\frac{2\cdot 3}{\beta_c}\eta_{\beta c}(t_2)) - \exp(\frac{2\cdot 3}{\beta_c}\eta_{\beta c}(t_3))} = \frac{t_1 - t_2}{t_2 - t_3}$$

9. A method according to claim 8, in which said sampling of polarization potential is carried out in such a way as to satisfy the following equation:

$$\eta_{\beta c}(t_2) - \eta_{\beta c}(t_1) = \eta_{\beta c}(t_3) - \eta_{\beta c}(t_2) = \Delta\eta_{\beta c},$$

and the Tafel slope $\beta_c$ is obtained by the following equation:

$$\beta_c = \frac{\Delta\eta_{\beta c}}{\log \frac{t_3 - t_2}{t_2 - t_1}}$$

10. A method according to claim 1, in which said Tafel slope $\beta_c$ of cathodic reaction is obtained by sampling from the variation of the polarization potential $\eta_{\beta c}(t)$ obtained as a function of time such polarization potentials $\eta_{\beta c}(t_1), \eta_{\beta c}(t_2), \eta_{\beta c}(t_3), \ldots \eta_{\beta c}(t_n)$ at times $t_1, t_2, t_3, \ldots t_n$ respectively as would satisfy the following equation:

$$\eta_{\beta c}(t_2) - \eta_{\beta c}(t_1) = \eta_{\beta c}(t_3) - \eta_{\beta c}(t_2) = \ldots$$
$$\eta_{\beta c}(t_n) - \eta_{\beta c}(t_{n-1}) = \Delta\eta_{\beta c},$$

and by using the following equation:

$$\beta_c = \Delta\eta_{\beta c}/\log \delta,$$

where $$\delta = \frac{1}{n-2}\left(\frac{t_3 - t_2}{t_2 - t_1} + \frac{t_4 - t_3}{t_3 - t_2} + \ldots + \frac{t_n - t_{n-1}}{t_{n-1} - t_{n-2}}\right)$$

11. A method according to claim 1, in which said predetermined polarization potential $\eta_{Rp}$ is $$-30_{mv} \leq \eta_{Rp} \leq +30_{mv}$$

12. A method according to claim 11, in which said predetermined polarization potential $\eta_{Rp}$ is $$-10_{mv} \leq \eta_{Rp} \leq 10_{mv}.$$

13. A method according to claim 1, in which said predetermined polarization potential $\eta_{\beta a}$ is 30 mV or more.

14. A method according to claim 13, in which the predetermined polarization potential $\eta_{\beta a}$ is $+50$ mV or more.

15. A method according to claim 1, in which said predetermined polarization potential $\eta_{\beta c}$ is $-30$ mV or lower.

16. A method according to claim 15, in which the predetermined polarization potential $\eta_{\beta c}$ is $-50$ mV or lower.

17. A method according to claim 1, in which after completion of any one of steps (A) to (C) a predetermined bias voltage is applied to said metal test piece, thereby bringing the potential of the test piece back to corrosion potential $E_{corr}$ before feeding a predetermined charge to the test piece.

18. A method according to claim 1, in which said corrosion current density $I_{corr}$ of the test piece is obtained by the following Equation:

$$I_{corr} = (K/2.3)/R_p, \text{ where } K = \beta_a\beta_c/(\beta_a + \beta_c).$$

19. A method according to claim 18, in which the corrosion rate V of the metal test piece is obtained by the following equation:

$$V = (M/Z \cdot F) \cdot I_{corr},$$

where M denotes the atomic weight of the test piece, Z the valence of the dissolved metal ion, and F the Faradaic constant.

* * * * *